United States Patent
Pettit et al.

(10) Patent No.: US 12,258,370 B2
(45) Date of Patent: *Mar. 25, 2025

(54) BETULASTATIN COMPOUNDS

(71) Applicant: Arizona Board of Regents on behalf of Arizona State University, Scottsdale, AZ (US)

(72) Inventors: George R. Pettit, Paradise Valley, AZ (US); Noeleen Melody, Mesa, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/166,008

(22) Filed: Feb. 8, 2023

(65) Prior Publication Data
US 2023/0192759 A1    Jun. 22, 2023

Related U.S. Application Data

(63) Continuation of application No. 16/762,781, filed as application No. PCT/US2018/060015 on Nov. 9, 2018, now Pat. No. 11,629,167.

(60) Provisional application No. 62/584,051, filed on Nov. 9, 2017.

(51) Int. Cl.
*C07J 63/00* (2006.01)
*A61P 35/00* (2006.01)
*C07J 71/00* (2006.01)

(52) U.S. Cl.
CPC ............. *C07J 63/008* (2013.01); *A61P 35/00* (2018.01); *C07J 71/0052* (2013.01)

(58) Field of Classification Search
CPC ........................... C07J 63/008; C07J 71/0052
See application file for complete search history.

(56) References Cited

PUBLICATIONS

Dorr et al. (Bioorganic & Medicinal Chemistry Letters, 2011, 21, 542-545).*

* cited by examiner

*Primary Examiner* — Susanna Moore
(74) *Attorney, Agent, or Firm* — Riverside Law LLP

(57) ABSTRACT

The present disclosure relates to Betulastatin compounds, pharmaceutical compositions and kits comprising such compounds, and methods for using such compounds or pharmaceutical compositions.

16 Claims, No Drawings

BETULASTATIN COMPOUNDS

CROSS-REFERENCE TO RELATED APPLICATIONS

The present application is a continuation of U.S. application Ser. No. 16/762,781, filed May 8, 2020, now allowed, which is a 35 U.S.C. § 371 National Phase Application from, and claiming priority to, International Application PCT/US2018/060015, filed Nov. 9, 2018, which claims the benefit of U.S. Provisional Application No. 62/584,051, filed Nov. 9, 2017, all of which applications are incorporated herein by reference in their entireties.

FEDERALLY SPONSORED RESEARCH OR DEVELOPMENT

This invention was made with government support under R01 CA090441 awarded by the National Institutes of Health. The government has certain rights in the invention.

BACKGROUND

Betulin a pentacyclic triterpene and its C-28 carboxylic acid derivative betulinic acid are well-known plant constituents especially in birch tree bark and in traditional medicine. Betulinic acid owing to the variety of medicinal properties and especially as a cancer cell growth inhibitor based on a mitochondrial mechanism of action continues to be widely studied.[2] Some of these advances have for example been extended to a clinical trial against dysplastic mole a potential precurser of melanoma. More broadly, betulinic acid has shown various levels of inhibition of growth in vitro against a variety of cancer types.[2] Early research in betulin chemistry explored structural modifications that included a betulin/betulinic acid series,[3] and earlier the α-apoallobetulin[4] and selected pentacyclic triterpenes oleanolic and uresolic acids.[5]

Citation of any reference in this section is not to be construed as an admission that such reference is prior art to the present disclosure.

SUMMARY

The present disclosure relates to Betulastatin compounds, pharmaceutical compositions comprising such compounds, kits, and methods for using such compounds or pharmaceutical compositions. The compounds have, or are believed to have, suitable cancer cell growth inhibition values.

In a first embodiment, the present disclosure provides a compound of formula (I):

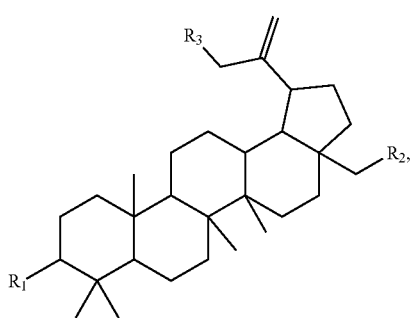

or a pharmaceutically acceptable salt thereof, wherein $R_1$ and $R_2$ are independently selected from OH, O—P(=O)OR'OR", O-Protecting Group, $R_4$ and $R_6$-$R_4$, wherein R' and R" are independently selected from the group consisting of lithium (Li+), sodium (Na+), potassium (K+), hydrogen (H), morpholine, quinine, tris(hydroxymethyl)aminomethane (TRIS), serine, and nitroarginine;

$R_3$ is H, $R_4$ or $R_6$-$R_4$;

$R_4$ is

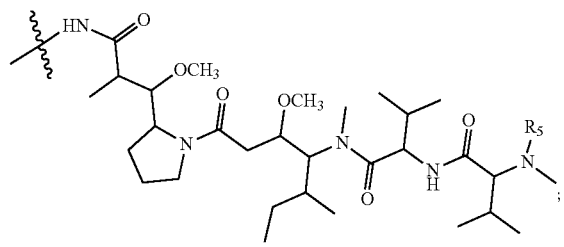

$R_5$ is H or $(C_1$-$C_6)$alkyl; and $R_6$ is $(C_1$-$C_6)$alkyl;

provided that one of $R_1$, $R_2$, and $R_3$ is $R_4$.

In a second embodiment, the present disclosure provides a compound of formula (II),

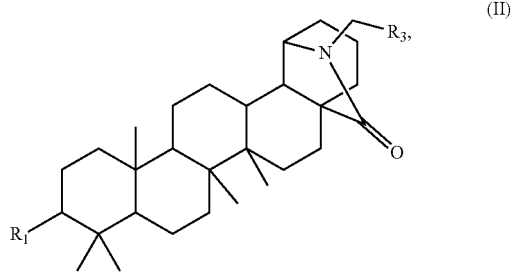

or a pharmaceutically acceptable salt thereof, wherein $R_1$ is OH, O—P(=O)OR'OR", or O-Protecting Group, wherein R' and R" are independently selected from the group consisting of lithium (Li+), sodium (Na+), potassium (K+), hydrogen (H), morpholine, quinine, tris(hydroxymethyl)aminomethane (TRIS), serine, and nitroarginine;

$R_3$ is $R_4$ or $R_6$-$R_4$;

$R_4$ is

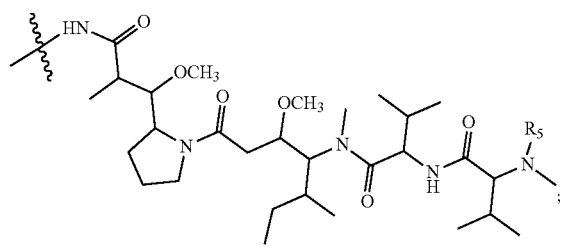

$R_5$ is H or $(C_1-C_6)$alkyl; and
$R_6$ is $(C_1-C_6)$alkyl.

DETAILED DESCRIPTION

The invention includes the following:
1. A compound of formula (I)

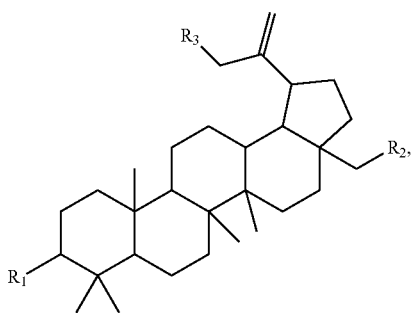

(I)

or a pharmaceutically acceptable salt thereof, wherein
$R_1$ and $R_2$ are independently selected from OH, O—P(=O)OR'OR", O-Protecting Group, $R_4$ and $R_6$-$R_4$, wherein R' and R" are independently selected from the group consisting of lithium (Li$^+$), sodium (Na$^+$), potassium (K$^+$), hydrogen (H), morpholine, quinine, tris(hydroxymethyl)aminomethane (TRIS), serine, and nitroarginine;
$R_3$ is H, $R_4$ or $R_6$-$R_4$;
$R_4$ is

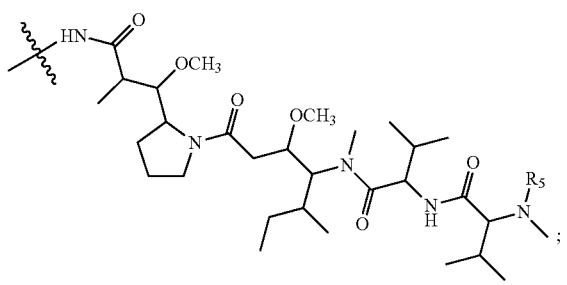

$R_5$ is H or $(C_1-C_6)$alkyl; and
$R_6$ is $(C_1-C_6)$alkyl;
provided that one of $R_1$, $R_2$, and $R_3$ is $R_4$.

2. The compound of the above 1, wherein $R_1$ is OH, OCOCH$_3$, O—P(=O)OR'OR", $R_4$ or $R_6$-$R_4$, wherein $R_6$ is $(C_1-C_3)$alkyl.

3. The compound of the above 1, wherein $R_1$ is OH or OCOCH$_3$.

4. The compound of the above 1, wherein $R_1$ is OH.

5. The compound of the above 1, wherein $R_1$ is OCOCH$_3$.

6. The compound of the above 1, wherein $R_1$ is $R_4$.

7. The compound of the above 1, wherein $R_1$ is $R_6$-$R_4$.

8. The compound of the above 1, 2 or 6, wherein $R_1$ is $R_4$ and $R_5$ is CH$_3$.

9. The compound of the above 1, 2 or 7, wherein $R_1$ is $R_6$-$R_4$, $R_6$ is $(C_2)$alkyl and $R_5$ is CH$_3$.

10. The compound of the above 1, wherein $R_2$ is OH, OCOCH$_3$, O—P(=O)OR'OR", $R_4$ or $R_6$-$R_4$ wherein $R_6$ is $(C_1-C_3)$alkyl.

11. The compound of the above 1, wherein $R_2$ is OH or OCOCH$_3$.

12. The compound of the above 1, wherein $R_2$ is OH.

13. The compound of the above 1, wherein $R_2$ is OCOCH$_3$.

14. The compound of the above 1, wherein $R_2$ is $R_4$.

15. The compound of the above 1, wherein $R_2$ is $R_6$-$R_4$.

16. The compound of the above 1, 10 or 14, wherein $R_2$ is $R_4$ and $R_5$ is CH$_3$.

17. The compound of the above 1, 10 or 15, wherein $R_2$ is $R_6$-$R_4$, $R_6$ is $(C_2)$alkyl and $R_5$ is CH$_3$.

18. The compound of the above 1, wherein $R_3$ is H.

19. The compound of the above 1, wherein $R_3$ is $R_4$.

20. The compound of the above 19, wherein $R_5$ is CH$_3$.

21. The compound of the above 1, wherein $R_3$ is $R_6$-$R_4$ and $R_6$ is $(C_2)$alkyl.

22. The compound of the above 21, wherein $R_5$ is CH$_3$.

23. The compound of the above 1, wherein the compound is:

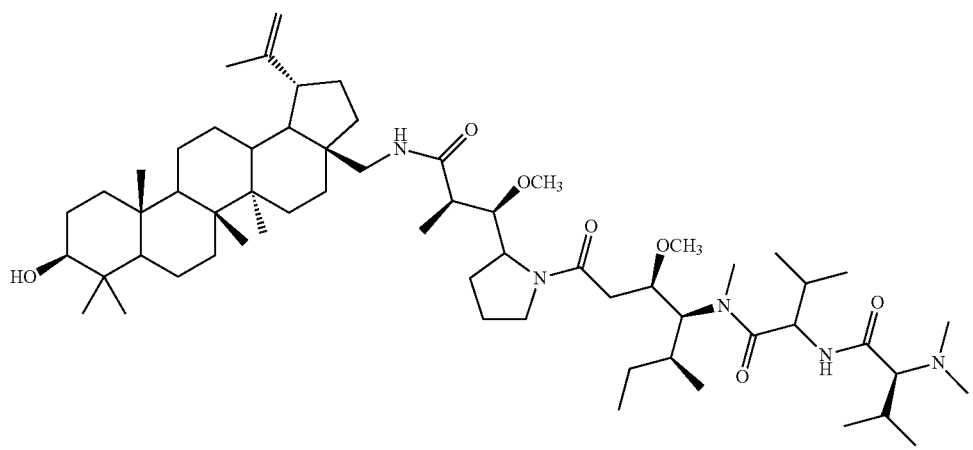 [SMILES: C=C(C)[C@@H]1CC[C@]2(CNC(=O)[C@H](C)[C@@H](OC)C3CCCN3C(=O)C[C@@H](OC)[C@H]([C@@H](C)CC)N(C)C(=O)C(NC(=O)[C@H](C(C)C)N(C)C)C(C)C)CC[C@]3(C)C(CCC4[C@@]5(C)CC[C@H](O)C(C)(C)C5CC[C@]43C)C12]

24. The compound of the above 1, wherein the compound is:

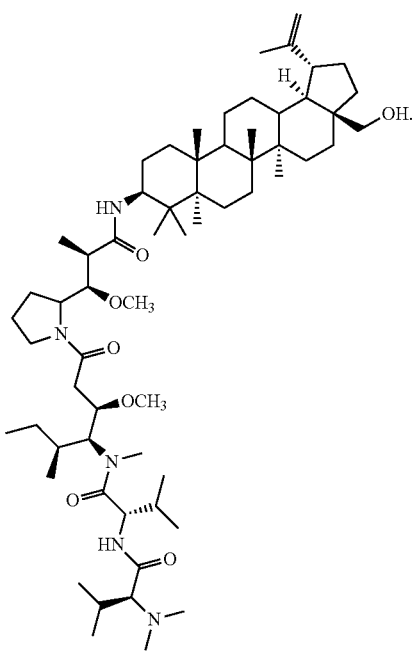

25. The compound of the above 1, wherein the compound is:

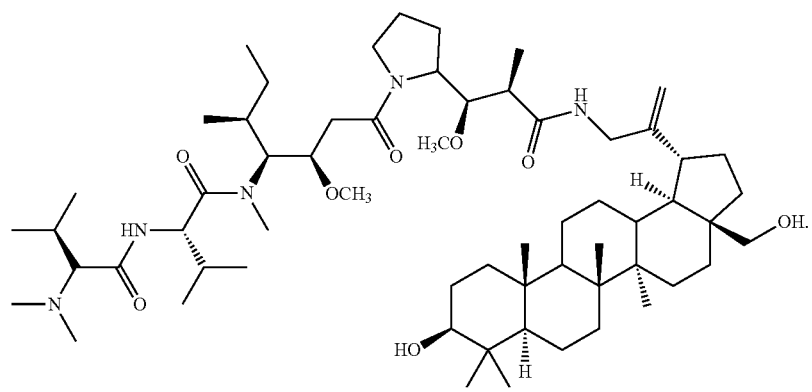

26. A compound of formula (II)

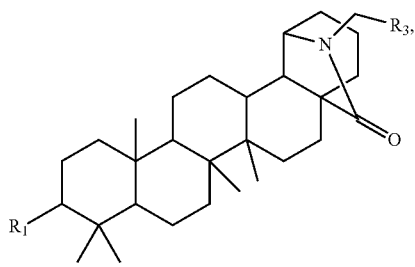
(II)

or a pharmaceutically acceptable salt thereof, wherein $R_1$ is OH, O—P(=O)OR'OR", or O-Protecting Group, wherein R' and R" are independently selected from the group consisting of lithium (Li$^+$), sodium (Na$^+$), potassium (K$^+$), hydrogen (H), morpholine, quinine, tris(hydroxymethyl)aminomethane (TRIS), serine, and nitroarginine;

$R_3$ is $R_4$ or $R_6$-$R_4$;

$R_4$ is

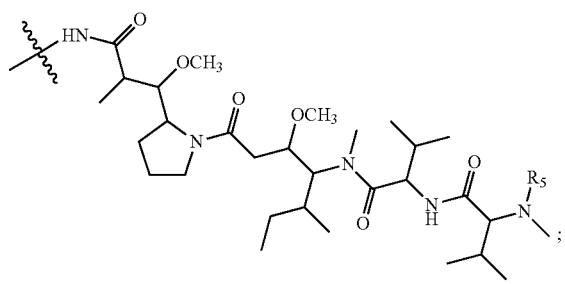

$R_5$ is H or $(C_1$-$C_6)$alkyl; and $R_6$ is $(C_1$-$C_6)$alkyl.

27. The compound of the above 26, wherein $R_1$ is OH or OCOCH$_3$.

28. The compound of the above 26, wherein $R_1$ is OH.

29. The compound of the above 26, wherein $R_1$ is OCOCH$_3$.

30. The compound of the above 26, wherein $R_3$ is $R_4$.

31. The compound of the above 30, wherein $R_5$ is CH$_3$.

32. The compound of the above 26, wherein $R_3$ is $R_6$-$R_4$.

33. The compound of the above 32, wherein $R_5$ is CH$_3$.

34. The compound of the above 26, wherein the compound is

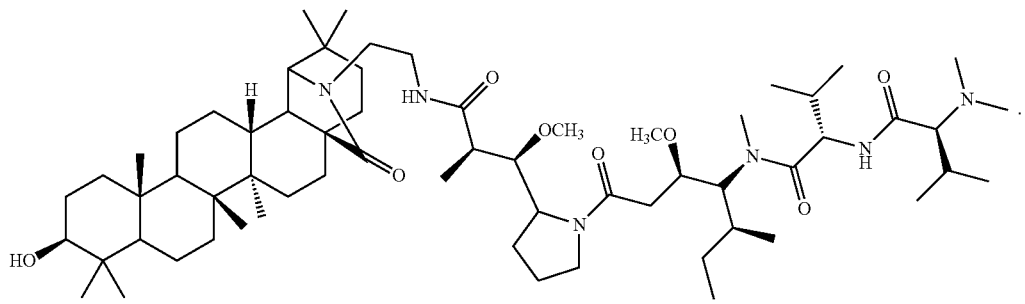

35. A pharmaceutical composition comprising a compound of any one of the above 1 to 34 or a pharmaceutically acceptable salt thereof and a pharmaceutically acceptable carrier.
36. A pharmaceutical composition comprising a combination of compounds of any one of the above 1 to 34 or pharmaceutically acceptable salts thereof and a pharmaceutically acceptable carrier.
37. The pharmaceutical composition of the above 35 or claim 36, further comprising a therapeutically effective amount of a second therapeutic agent selected from the group consisting of a tubulin-forming inhibitor, a topoisomerase inhibitor, and a DNA binder.
38. A method for killing or inhibiting the proliferation of tumor cells or cancer cells comprising treating the tumor cells or cancer cells with a compound of any of the above 1 to 34, or a pharmaceutical composition of the above 36 or 37, in an amount effective to kill or inhibit the proliferation of the tumor cells or cancer cells.
39. A method for treating cancer in a patient in need thereof comprising administering to the patient a compound of the above claims 1 to 34, or a pharmaceutical composition of the above 36 or 37, wherein the compound or pharmaceutical composition is administered in an amount effective to treat cancer.
40. The method of the above 39, further comprising administering an effective amount of a second therapeutic agent.
41. The method of the above 39, wherein the cancer is selected from the group consisting of breast cancer, ovarian cancer, stomach cancer, endometrial cancer, salivary gland cancer, lung cancer, kidney cancer, colon cancer, colorectal cancer, thyroid cancer, pancreatic cancer, prostate cancer, bladder cancer and central nervous system cancer.
42. The method of the above 41, wherein the cancer is selected from the group consisting of breast cancer, lung cancer, colon cancer, pancreatic cancer, prostate cancer and central nervous system cancer.
43. A method of determining inhibition of cellular proliferation by a compound, comprising contacting cells in a cell culture medium with the compound of any of the above 1 to 34 and measuring the cytotoxic activity of the compound, whereby proliferation of the cells is inhibited.
44. A use of the compound of any of the above 1 to 34 in the manufacture of a medicament for treating cancer.
45. A compound of any one of the above 1 to 34 or a pharmaceutical composition of the above 36 or 37 for use in treating cancer.
46. An article of manufacture comprising the compound of any of the above 1 to 34, a container, and a package insert or label indicating that the compound can be used to treat cancer.

DEFINITIONS

Unless defined otherwise, all technical and scientific terms used herein have the same meaning as those commonly understood by one of ordinary skill in the art to which this invention belongs. Although methods and materials similar or equivalent to those described herein can be used in the practice or testing of the present disclosure, suitable methods and materials are described below. The materials, methods and examples are illustrative only, and are not intended to be limiting. All publications, patents and other documents mentioned herein are incorporated by reference in their entirety.

Throughout this specification, the word "comprise" or variations such as "comprises" or "comprising" will be understood to imply the inclusion of a stated integer or groups of integers but not the exclusion of any other integer or group of integers.

The term "a" or "an" may mean more than one of an item.

The terms "and" and "or" may refer to either the conjunctive or disjunctive and mean "and/or".

The term "about" means within plus or minus 10% of a stated value. For example, "about 100" would refer to any number between 90 and 110.

The phrase "pharmaceutically acceptable salt," as used herein, refers to pharmaceutically acceptable organic or inorganic salts of a compound of the disclosure. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

The term "pharmaceutically acceptable carrier" refers to a diluent, adjuvant or excipient, with which a compound of the disclosure may be administered. Pharmaceutically acceptable carriers include any and all solvents, diluents, or other liquid vehicles, dispersions or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the disclosure such as by producing any undesirable biological effect or otherwise interacting in a deleterious manner with any other component(s) of the pharmaceutically acceptable composition, its use is contemplated to be within the scope of this disclosure. Examples of pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols, such a propylene glycol or polyethylene glycol; esters, such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The term "therapeutically effective amount" refers to an amount of a compound of the disclosure or a pharmaceutically acceptable salt thereof effective to treat a cancer in a patient. For purposes of this disclosure, the therapeutically effective amount of the compound may reduce the number of cancer cells; reduce the tumor size; reduce to some extent cancer cell infiltration into peripheral organs, tumor metastasis or tumor growth; and/or relieve to some extent one or more of the symptoms associated with the cancer.

The terms "treat" or "treatment" refer to therapeutic treatment and prophylactic measures to obtain a beneficial or desired result. For purposes of this disclosure, beneficial or desired results include, but are not limited to, alleviation of symptoms, diminishment of extent of disease, stabilized (i.e., not worsening) state of disease, delay or slowing of disease progression, amelioration or palliation of the disease state, remission (whether partial or total), whether detectable or undetectable and prevention of relapse. "Treatment" can also include prolonging survival as compared to expected survival if not receiving treatment. Those in need of treatment include those already having the condition or disorder as well as those prone to have the condition or disorder.

The terms "cancer" and "cancerous" refer to or describe the physiological condition or disorder in mammals that is typically characterized by unregulated cell growth. A "tumor" comprises one or more cancerous cells.

Exemplary cancers include, but not limited to, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophogeal cancer, stomach cancer, oral cancer, nasal cancer, throat cancer, central nervous system cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, retinoblastoma, acute lymphoblastic leukemia (ALL), acute lymphoblastic B-cell leukemia, acute lymphoblastic T-cell leukemia, acute myeloblastic leukemia (AML), acute promyelocytic leukemia (APL), acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia (CML), chronic lymphocytic leukemia (CLL), hairy cell leukemia, multiple myeloma, Hodgkin's disease, non-Hodgkin's lymphoma, Waldenstrom's macroglobulinemia, heavy chain disease and polycythemia vera.

The term "cytotoxic activity" refers to a cell-killing, a cytostatic or an anti-proliferative effect of a compound of the disclosure. Methods for measuring cytotoxic activity are well-known in the art. Cytotoxic activity may be expressed as the $IC_{50}$ value, which is the concentration (molar or mass) per unit volume at which half the cells survive.

The term "patient," as used herein, includes, but is not limited to, a human, rat, mouse, guinea pig, monkey, pig, goat, cow, horse, dog, cat, bird and fowl. In some embodiments, the patient is a human.

The term "($C_1$-$C_6$) alkyl" refers to saturated linear or branched hydrocarbon structures having 1, 2, 3, 4, 5, or 6 carbon atoms. When an alkyl residue having a specific number of carbons is named, all geometric isomers having that number of carbons are intended to be encompassed; thus, for example, "propyl" includes n-propyl and iso-propyl and "butyl" includes n-butyl, sec-butyl, iso-butyl and tert-butyl. Examples of "($C_1$-$C_6$) alkyl groups include methyl, ethyl, n-propyl, iso-propyl, n-butyl, tert-butyl, n-pentyl, n-hexyl, and the like.

The term "($C_1$-$C_3$) alkyl" refers to saturated linear or branched hydrocarbon structures having 1, 2 or 3 carbon atoms. When an alkyl residue having a specific number of carbons is named, all geometric isomers having that number of carbons are intended to be encompassed; thus, for example, "propyl" includes n-propyl and iso-propyl. Examples of "($C_1$-$C_3$) alkyl groups include methyl, ethyl, n-propyl and iso-propyl.

The term "Protecting Group" refers to any group that is capable of reversibly protecting another functional group from undergoing an undesired reaction. Suitable oxygen and nitrogen protecting groups, as well as suitable conditions for protection and deprotection are well-known in the art and are described e.g., in T. W. Greene and P. G. M. Wuts, "Protective Groups in Organic Synthesis", Third edition, Wiley, New York 1999, and references cited therein. Representative hydroxy protecting groups include acetates (e.g., pivaloate and benzoate), benzyl ether, p-methoxybenzyl ether, trityl ether, tetrahydropyranyl ether, trialkylsilyl ethers (e.g., trimethylsilyl ether, triethylsilyl ether, triisopropyl silyl ether, t-butyldimethyl silyl ether, triphenylmethyl silyl ether), allyl ethers, methoxymethyl ether, 2-methoxyethoxymethyl ether, methanesulfonate and p-toluenesulfonate. Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like.

A compound of the disclosure can contain one, two, or more asymmetric centers and thus can give rise to enantiomers, diastereomers, and other stereoisomeric forms. The disclosure encompasses compounds with all such possible forms, as well as their racemic and resolved forms or any mixture thereof, unless specifically otherwise indicated. When a compound of the disclosure contains an olefinic double bond, a C=N double bond, or any other center of geometric asymmetry, it is intended to include all "geometric isomers", e.g., both Z and E geometric isomers, unless specifically otherwise indicated. All "tautomers", e.g., amine-imine, enamine-enimine, enamine-imine, urea-isourea, ketone-enol, amide-imidic acid, lactam-lactim, are intended to be encompassed by the disclosure as well unless specifically otherwise indicated.

Compounds of Formula (I)

In one embodiment, the present disclosure provides a compound of formula (I):

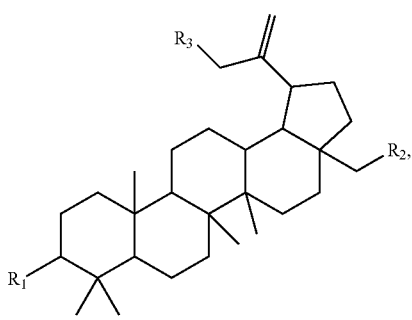

(I)

or a pharmaceutically acceptable salt thereof, wherein $R_1$ and $R_2$ are independently selected from OH, O—P(=O)OR'OR", O-Protecting Group, $R_4$ and $R_6$-$R_4$, wherein R' and R" are independently selected from the group consisting of lithium ($Li^+$), sodium ($Na^+$), potassium ($K^+$), hydrogen (H), morpholine, quinine, tris(hydroxymethyl)aminomethane (TRIS), serine, and nitroarginine;

$R_3$ is H, $R_4$ or $R_6$-$R_4$;

$R_4$ is

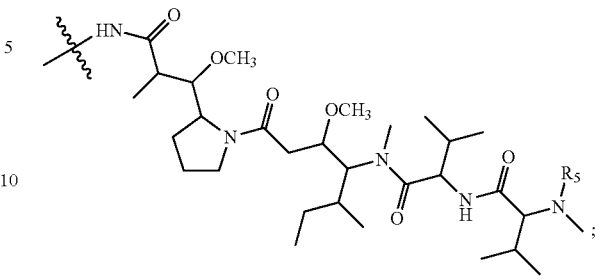

$R_5$ is H or $(C_1\text{-}C_6)$alkyl; and
$R_6$ is $(C_1\text{-}C_6)$alkyl;
provided that one of $R_1$, $R_2$, and $R_3$ is $R_4$.

In one embodiment, $R_1$ is OH, $OCOCH_3$, O—P(=O)OR'OR", $R_4$ or $R_6$-$R_4$, wherein $R_6$ is $(C_1\text{-}C_3)$alkyl. In another embodiment, $R_1$ is OH, $OCOCH_3$, O—P(=O)OR'OR", or $R_4$. In another embodiment, $R_1$ is OH, $OCOCH_3$ or $R_4$. In another embodiment, $R_1$ is OH, $OCOCH_3$, $R_4$ or $R_6$-$R_4$, wherein $R_6$ is $(C_1\text{-}C_3)$alkyl. In another embodiment, $R_1$ is OH or $OCOCH_3$. In another embodiment, $R_1$ is OH. In another embodiment, $R_1$ is $OCOCH_3$. In another embodiment, $R_1$ is $R_4$. In another embodiment, $R_1$ is $R_4$ and $R_5$ is $CH_3$. In another embodiment, $R_1$ is $R_4$ and $R_5$ is H.

In another embodiment, $R_1$ is $R_6$-$R_4$, wherein $R_6$ is $(C_1\text{-}C_3)$alkyl. In another embodiment, $R_1$ is $R_6$-$R_4$, wherein $R_6$ is $(C_1)$alkyl. In another embodiment, $R_1$ is $R_6$-$R_4$, wherein $R_6$ is $(C_2)$alkyl. In another embodiment, $R_1$ is $R_6$-$R_4$, wherein $R_6$ is $(C_3)$alkyl.

In another embodiment, $R_1$ is $R_6$-$R_4$, wherein $R_6$ is $(C_1\text{-}C_3)$alkyl and $R_5$ is $CH_3$. In another embodiment, $R_1$ is $R_6$-$R_4$, wherein $R_6$ is $(C_1\text{-}C_3)$alkyl and $R_5$ is H. In another embodiment, $R_1$ is $R_6$-$R_4$, wherein $R_6$ is $(C_1)$alkyl and $R_5$ is $CH_3$. In another embodiment, $R_1$ is $R_6$-$R_4$, wherein $R_6$ is $(C_1)$alkyl and $R_5$ is H. In another embodiment, $R_1$ is $R_6$-$R_4$, wherein $R_6$ is $(C_2)$alkyl and $R_5$ is $CH_3$. In another embodiment, $R_1$ is $R_6$-$R_4$, wherein $R_6$ is $(C_2)$alkyl and $R_5$ is H. In another embodiment, $R_1$ is $R_6$-$R_4$, wherein $R_6$ is $(C_3)$alkyl and $R_5$ is $CH_3$. In another embodiment, $R_1$ is $R_6$-$R_4$, wherein $R_6$ is $(C_3)$alkyl and $R_5$ is H.

In one embodiment, $R_2$ is OH, $OCOCH_3$, O—P(=O)OR'OR", $R_4$ or $R_6$-$R_4$, wherein $R_6$ is $(C_1\text{-}C_3)$alkyl. In another embodiment, $R_2$ is OH, $OCOCH_3$, O—P(=O)OR'OR", or $R_4$. In another embodiment, $R_2$ is OH, $OCOCH_3$ or $R_4$. In another embodiment, $R_2$ is OH, $OCOCH_3$, $R_4$ or $R_6$-$R_4$, wherein $R_6$ is $(C_1\text{-}C_3)$alkyl. In another embodiment, $R_2$ is OH or $OCOCH_3$. In another embodiment, $R_2$ is OH. In another embodiment, $R_2$ is $OCOCH_3$. In another embodiment, $R_2$ is $R_4$. In another embodiment, $R_2$ is $R_4$ and $R_5$ is $CH_3$. In another embodiment, $R_2$ is $R_4$ and $R_5$ is H.

In another embodiment, $R_2$ is $R_6$-$R_4$, wherein $R_6$ is $(C_1\text{-}C_3)$alkyl. In another embodiment, $R_2$ is $R_6$-$R_4$, wherein $R_6$ is $(C_1)$alkyl. In another embodiment, $R_2$ is $R_6$-$R_4$, wherein $R_6$ is $(C_2)$alkyl. In another embodiment, $R_2$ is $R_6$-$R_4$, wherein $R_6$ is $(C_3)$alkyl.

In another embodiment, $R_2$ is $R_6$-$R_4$, wherein $R_6$ is $(C_1\text{-}C_3)$alkyl and $R_5$ is $CH_3$. In another embodiment, $R_2$ is $R_6$-$R_4$, wherein $R_6$ is $(C_1\text{-}C_3)$alkyl and $R_5$ is H. In another embodiment, $R_2$ is $R_6$-$R_4$, wherein $R_6$ is $(C_1)$alkyl and $R_5$ is $CH_3$. In another embodiment, $R_2$ is $R_6$-$R_4$, wherein $R_6$ is $(C_1)$alkyl and $R_5$ is H. In another embodiment, $R_2$ is $R_6$-$R_4$, wherein $R_6$ is $(C_2)$alkyl and $R_5$ is $CH_3$. In another embodiment, $R_2$ is $R_6$-$R_4$, wherein $R_6$ is $(C_2)$alkyl and $R_5$ is H. In another embodiment, $R_2$ is $R_6$-$R_4$, wherein $R_6$ is $(C_3)$alkyl and $R_5$ is $CH_3$. In another embodiment, $R_2$ is $R_6$-$R_4$, wherein $R_6$ is $(C_3)$alkyl and $R_5$ is H.

In one embodiment, $R_3$ is H or $R_4$. In another embodiment, $R_3$ is H or $R_6$-$R_4$. In another embodiment, $R_3$ is $R_4$ or $R_6$-$R_4$. In another embodiment, $R_3$ is H. In another embodiment, $R_3$ is $R_4$. In another embodiment, $R_3$ is $R_4$ and $R_5$ is $CH_3$. In another embodiment, $R_3$ is $R_4$ and $R_5$ is H.

In another embodiment, $R_3$ is $R_6$-$R_4$, wherein $R_6$ is $(C_1$-$C_3)$alkyl. In another embodiment, $R_3$ is $R_6$-$R_4$, wherein $R_6$ is $(C_1)$alkyl. In another embodiment, $R_3$ is $R_6$-$R_4$, wherein $R_6$ is $(C_2)$alkyl. In another embodiment, $R_3$ is $R_6$-$R_4$, wherein $R_6$ is $(C_3)$alkyl.

In another embodiment, $R_3$ is $R_6$-$R_4$, wherein $R_6$ is $(C_1$-$C_3)$alkyl and $R_5$ is $CH_3$. In another embodiment, $R_3$ is $R_6$-$R_4$, wherein $R_6$ is $(C_1$-$C_3)$alkyl and $R_5$ is H. In another embodiment, $R_3$ is $R_6$-$R_4$, wherein $R_6$ is $(C_1)$alkyl and $R_5$ is $CH_3$. In another embodiment, $R_3$ is $R_6$-$R_4$, wherein $R_6$ is $(C_1)$alkyl and $R_5$ is H. In another embodiment, $R_3$ is $R_6$-$R_4$, wherein $R_6$ is $(C_2)$alkyl and $R_5$ is $CH_3$. In another embodiment, $R_3$ is $R_6$-$R_4$, wherein $R_6$ is $(C_2)$alkyl and $R_5$ is H. In another embodiment, $R_3$ is $R_6$-$R_4$, wherein $R_6$ is $(C_3)$alkyl and $R_5$ is $CH_3$. In another embodiment, $R_3$ is $R_6$-$R_4$, wherein $R_6$ is $(C_3)$alkyl and $R_5$ is H.

In another embodiment, the present disclosure provides a compound of formula (II),

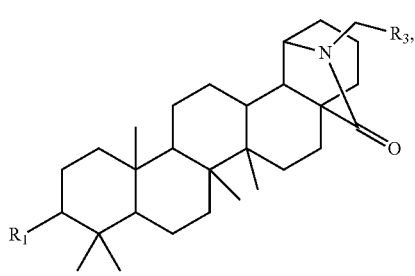

(II)

or a pharmaceutically acceptable salt thereof, wherein
$R_1$ is OH, O—P(=O)OR'OR", or O-Protecting Group, wherein R' and R" are independently selected from the group consisting of lithium (Li$^+$), sodium (Na$^+$), potassium (K$^+$), hydrogen (H), morpholine, quinine, tris (hydroxymethyl)aminomethane (TRIS), serine, and nitroarginine;
$R_3$ is $R_4$ or $R_6$-$R_4$;
$R_4$ is

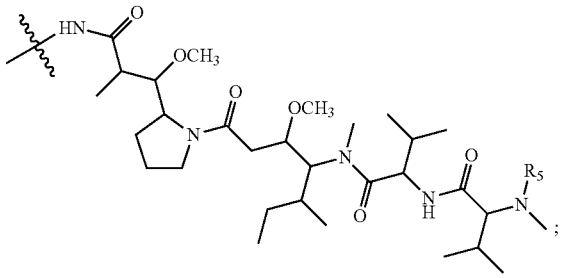

$R_5$ is H or $(C_1$-$C_6)$alkyl; and
$R_6$ is $(C_1$-$C_6)$alkyl.

In one embodiment, $R_1$ is OH, OCOCH$_3$, or O—P(=O)OR'OR". In another embodiment, $R_1$ is OH, OCOCH$_3$, or O—P(=O)OR'OR". In another embodiment, $R_1$ is OH or OCOCH$_3$. In another embodiment, $R_1$ is OH. In another embodiment, $R_1$ is OCOCH$_3$.

In one embodiment, $R_3$ is $R_4$. In another embodiment, $R_3$ is $R_4$ and $R_5$ is $CH_3$. In another embodiment, $R_3$ is $R_4$ and $R_5$ is H.

In another embodiment, $R_3$ is $R_6$-$R_4$. In another embodiment, $R_3$ is $R_6$-$R_4$, wherein $R_6$ is $(C_1$-$C_3)$alkyl. In another embodiment, $R_3$ is $R_6$-$R_4$, wherein $R_6$ is $(C_1)$alkyl. In another embodiment, $R_3$ is $R_6$-$R_4$, wherein $R_6$ is $(C_2)$alkyl. In another embodiment, $R_3$ is $R_6$-$R_4$, wherein $R_6$ is $(C_3)$alkyl.

In another embodiment, $R_3$ is $R_6$-$R_4$, wherein $R_6$ is $(C_1$-$C_3)$alkyl and $R_5$ is $CH_3$. In another embodiment, $R_3$ is $R_6$-$R_4$, wherein $R_6$ is $(C_1$-$C_3)$alkyl and $R_5$ is H. In another embodiment, $R_3$ is $R_6$-$R_4$, wherein $R_6$ is $(C_1)$alkyl and $R_5$ is $CH_3$. In another embodiment, $R_3$ is $R_6$-$R_4$, wherein $R_6$ is $(C_1)$alkyl and $R_5$ is H. In another embodiment, $R_3$ is $R_6$-$R_4$, wherein $R_6$ is $(C_2)$alkyl and $R_5$ is $CH_3$. In another embodiment, $R_3$ is $R_6$-$R_4$, wherein $R_6$ is $(C_2)$alkyl and $R_5$ is H. In another embodiment, $R_3$ is $R_6$-$R_4$, wherein $R_6$ is $(C_3)$alkyl and $R_5$ is $CH_3$. In another embodiment, $R_3$ is $R_6$-$R_4$, wherein $R_6$ is $(C_3)$alkyl and $R_5$ is H.

Representative compounds of formula (I) and formula (II) include:

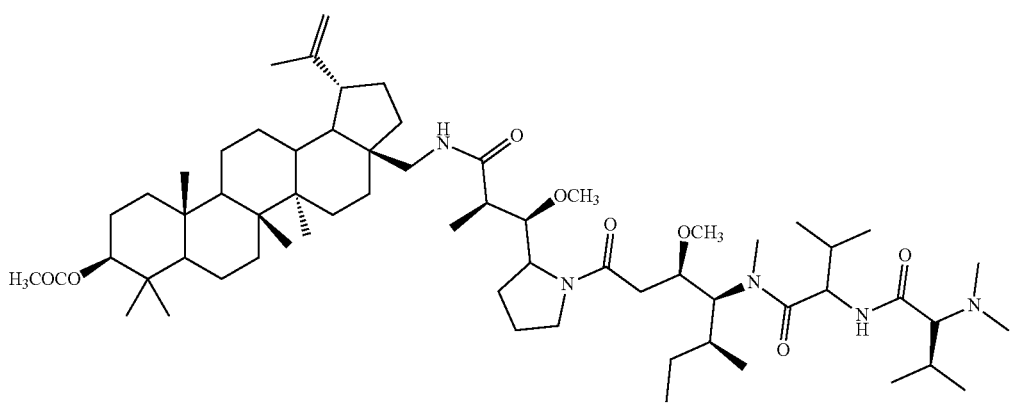

-continued
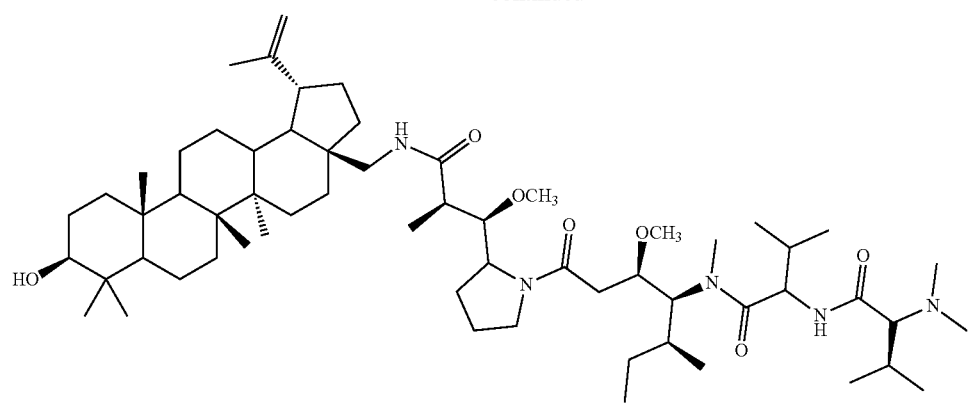
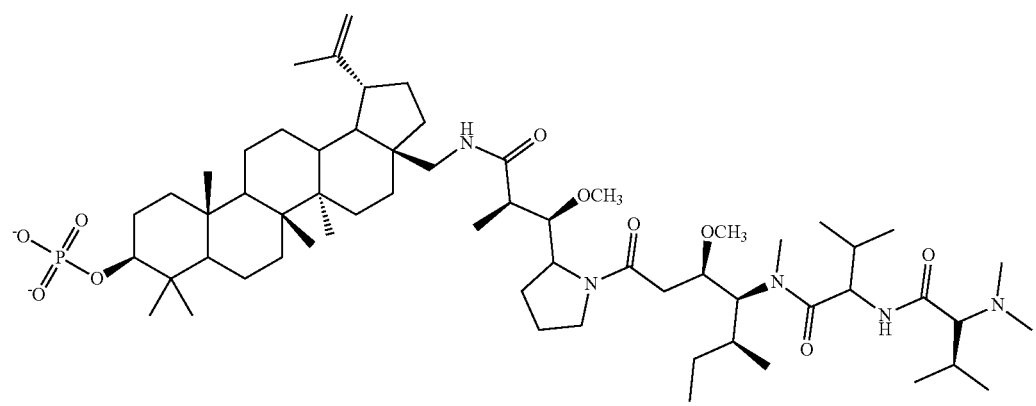
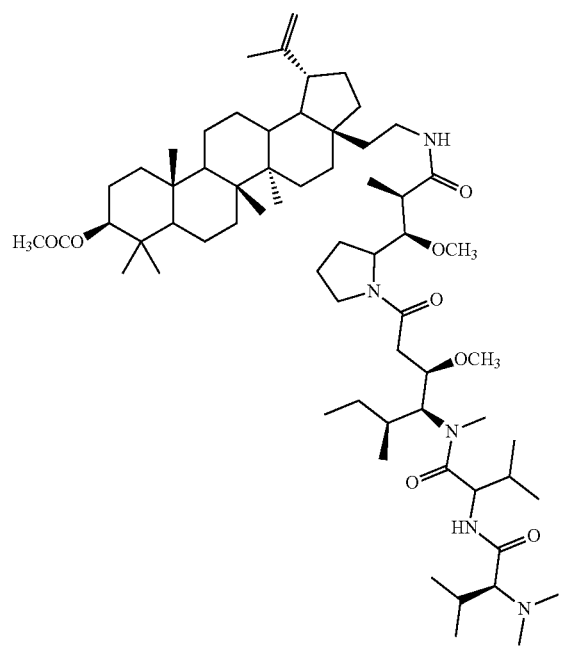

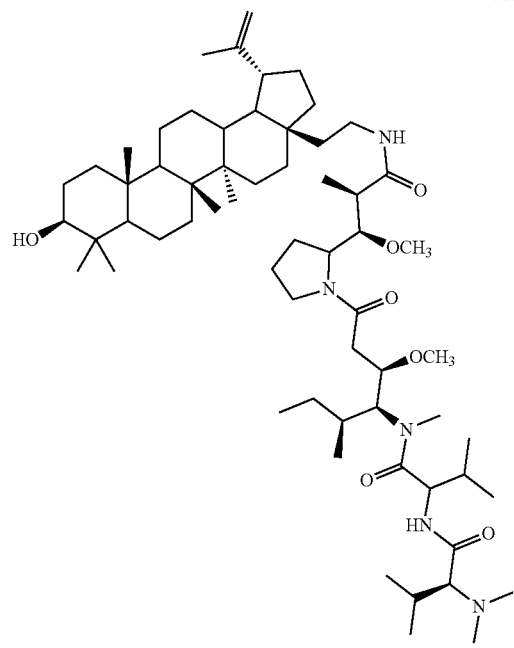
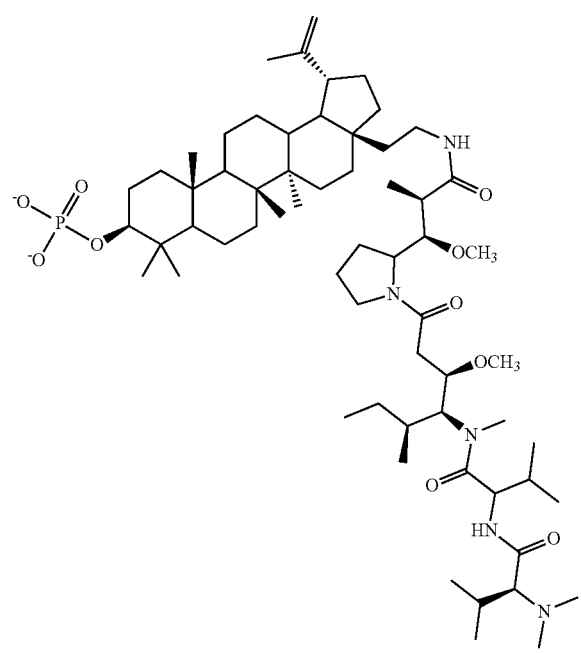

-continued
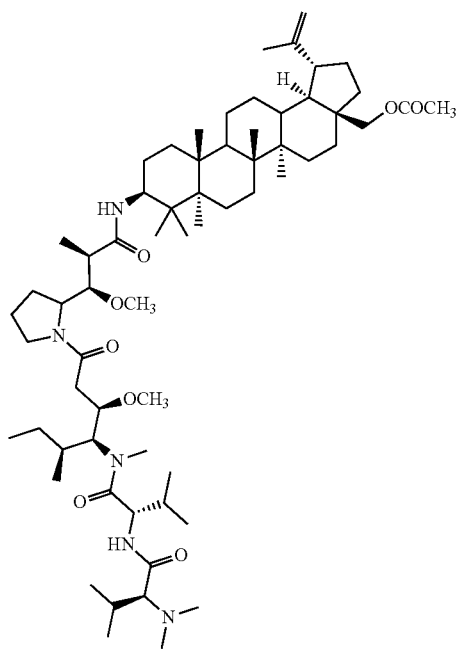
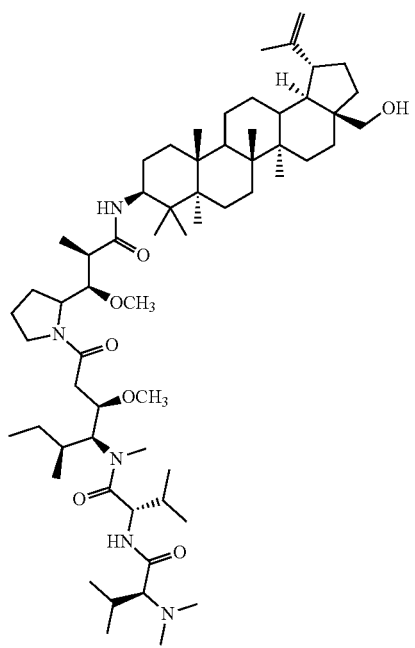

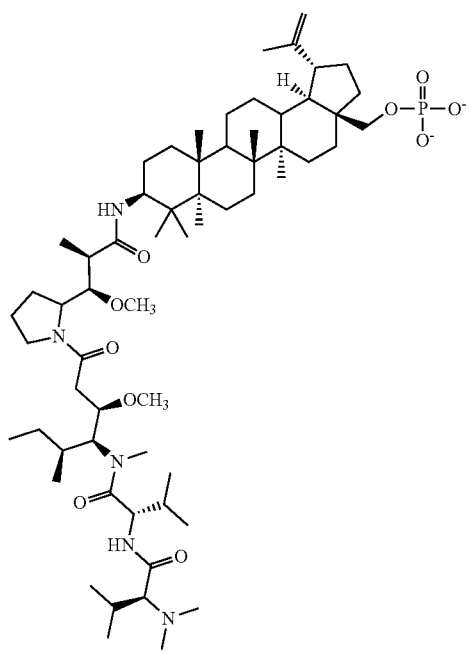
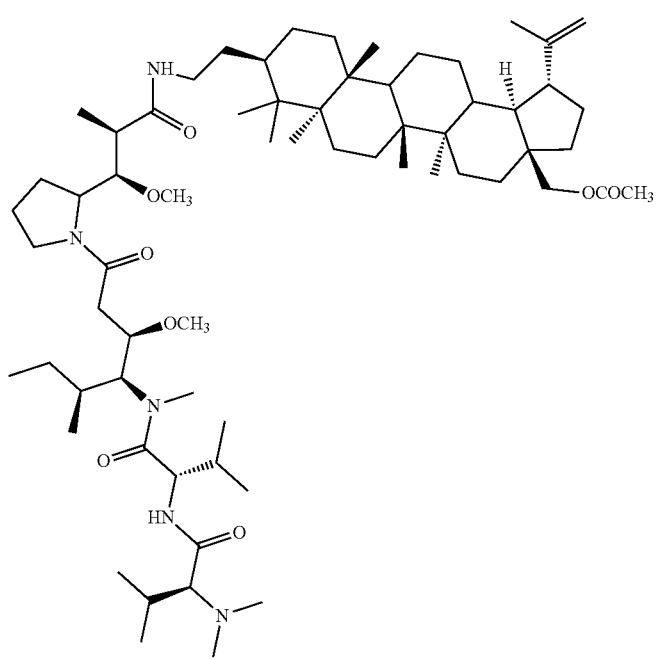

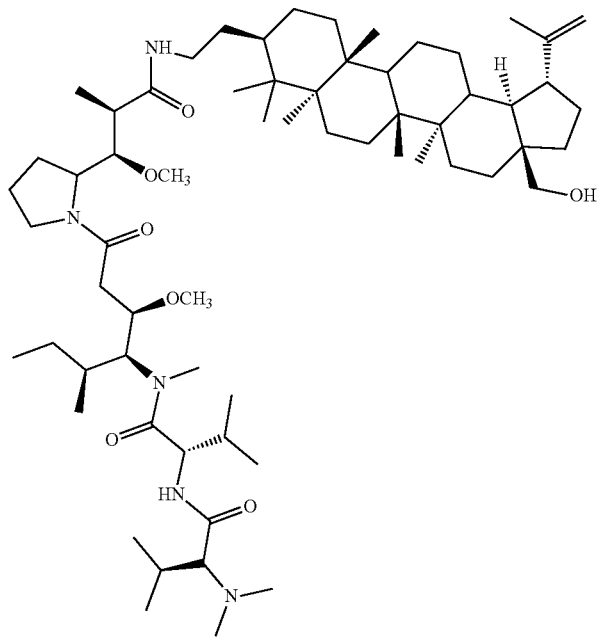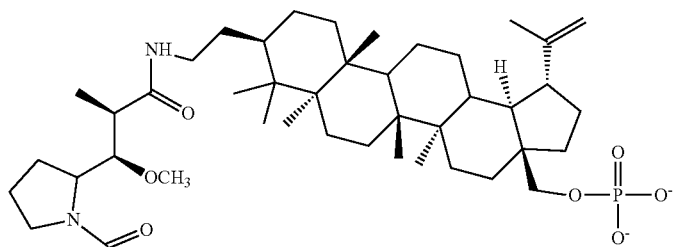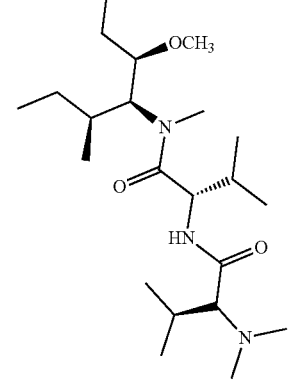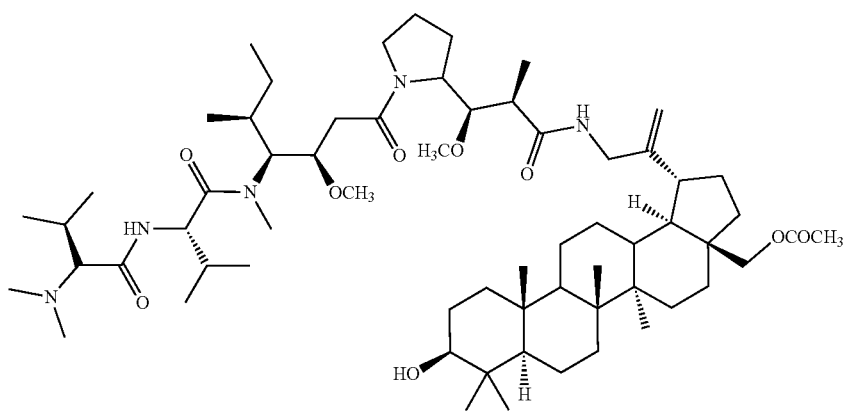

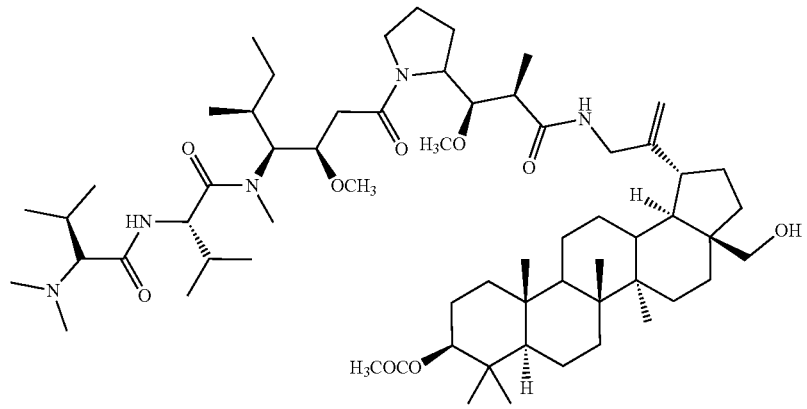
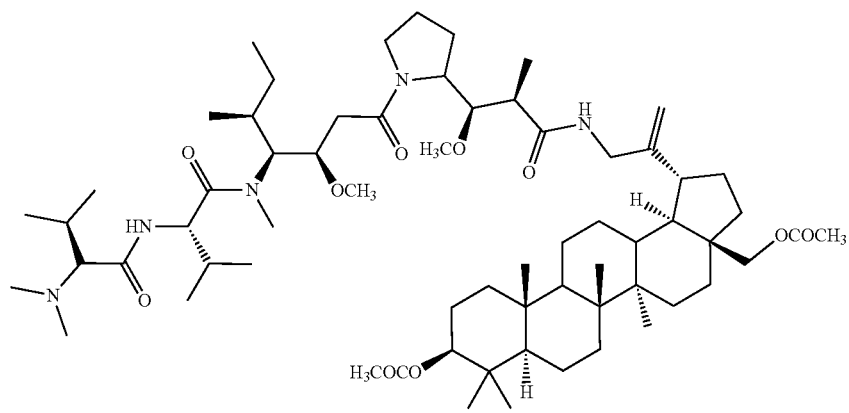
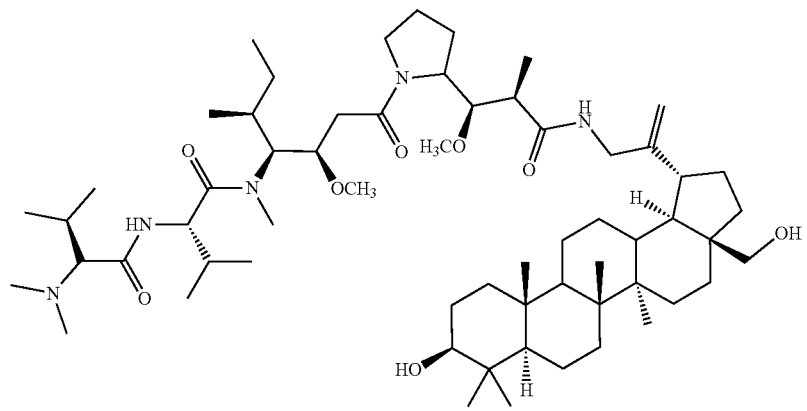
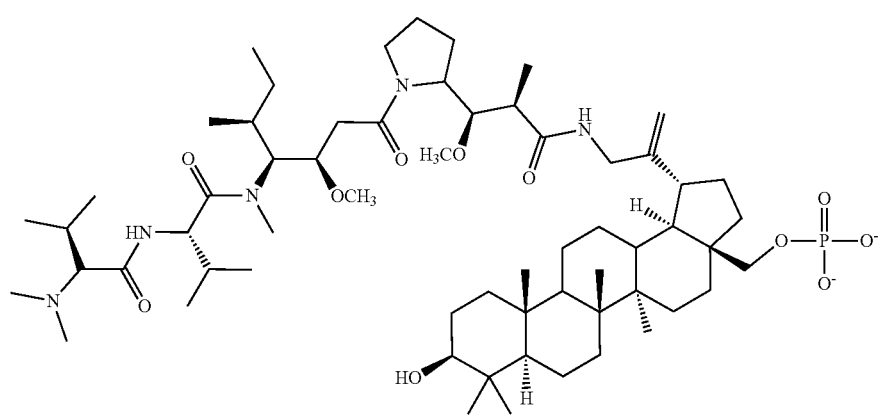

-continued
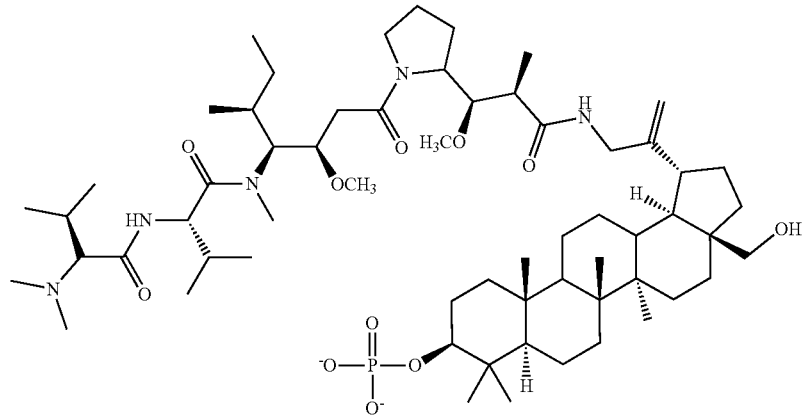
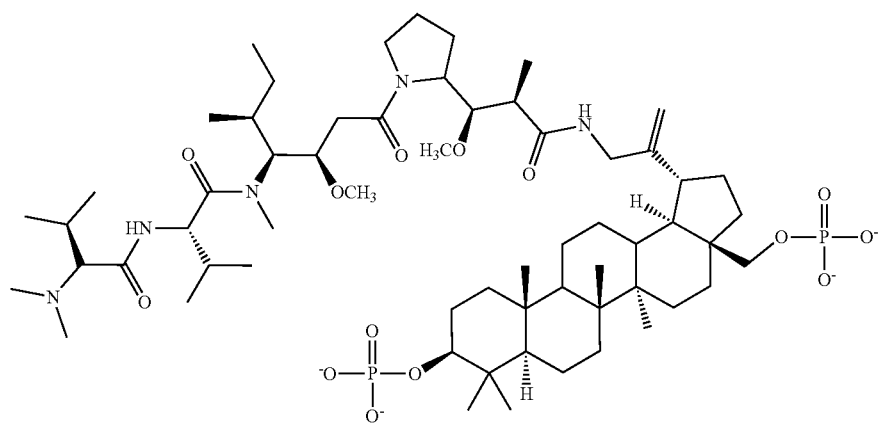
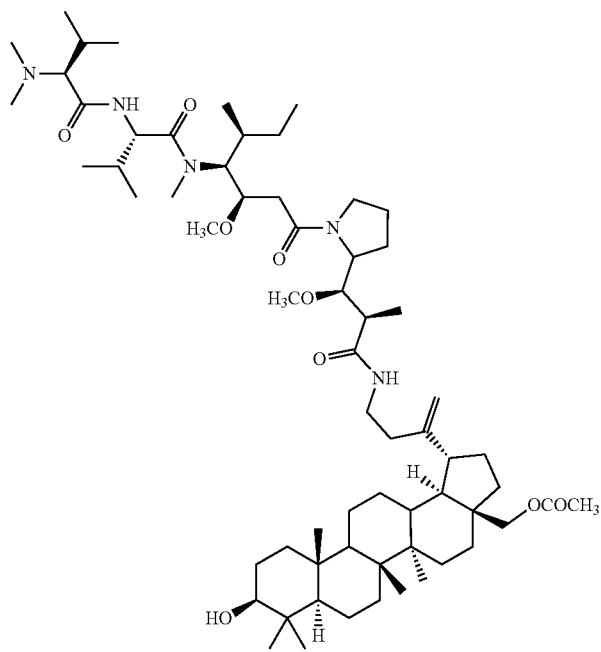

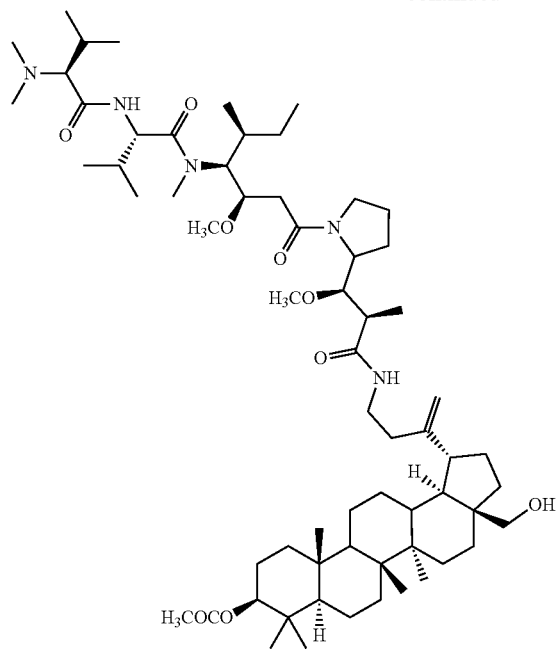
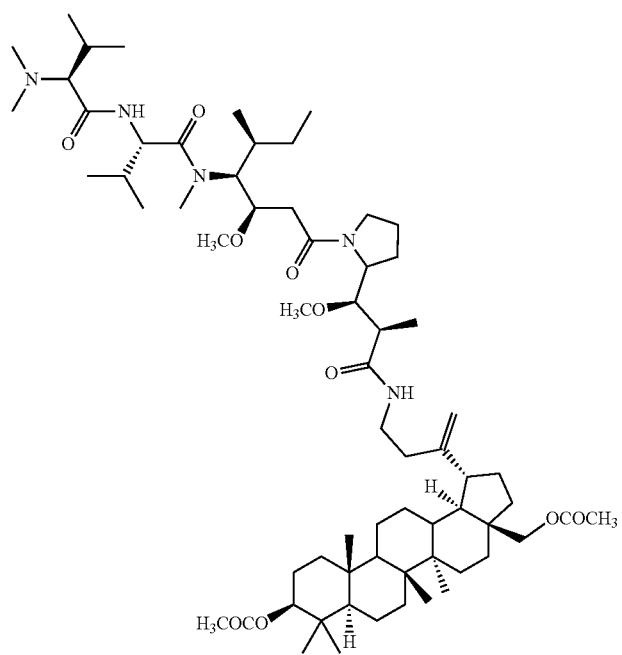

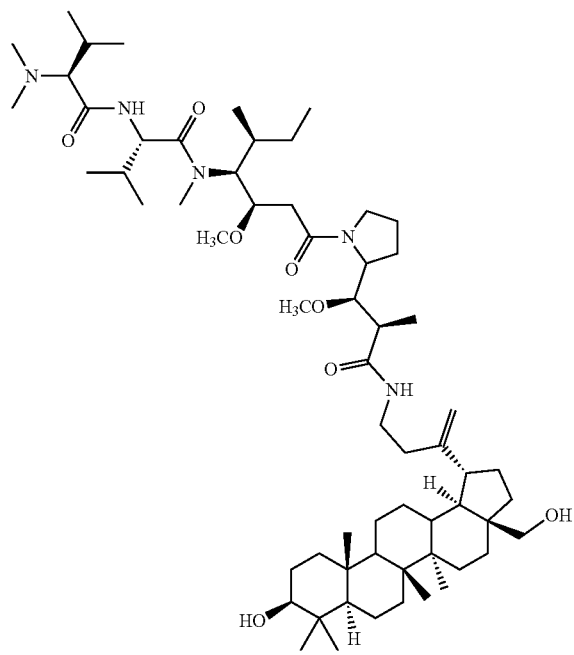
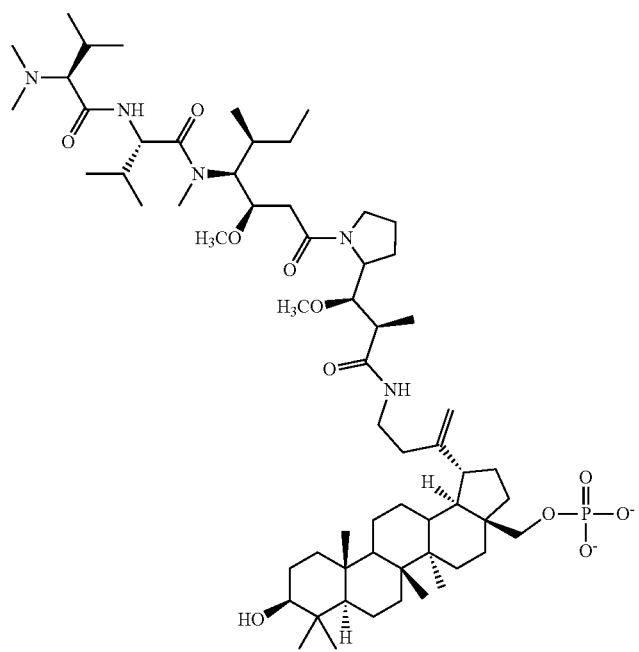

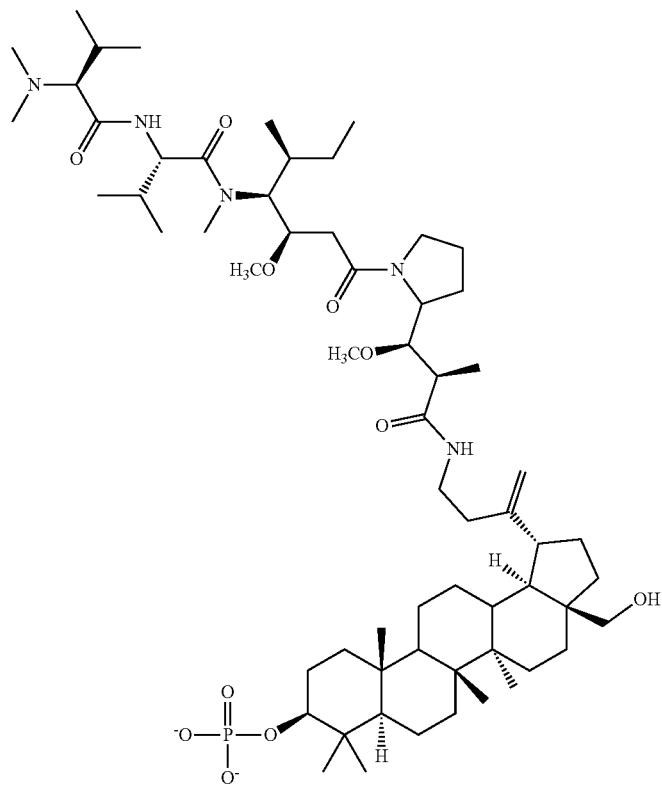
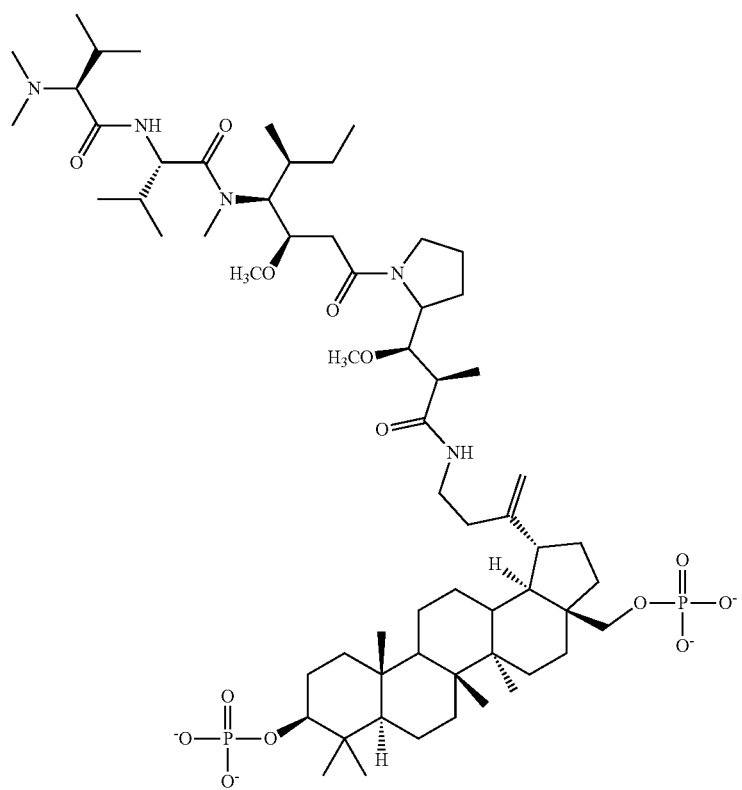

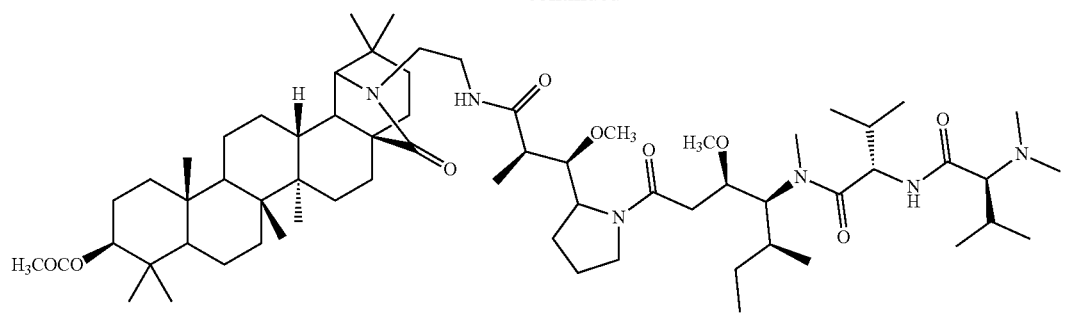
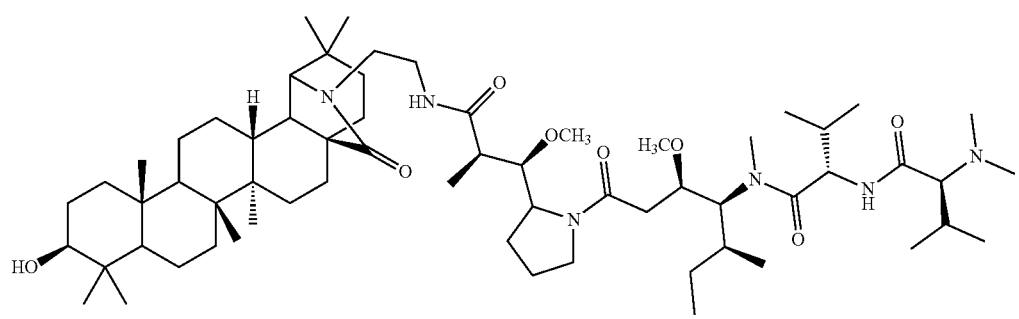
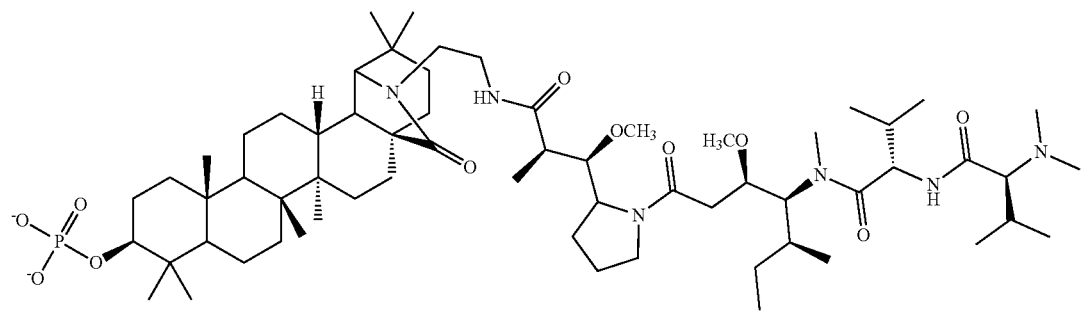
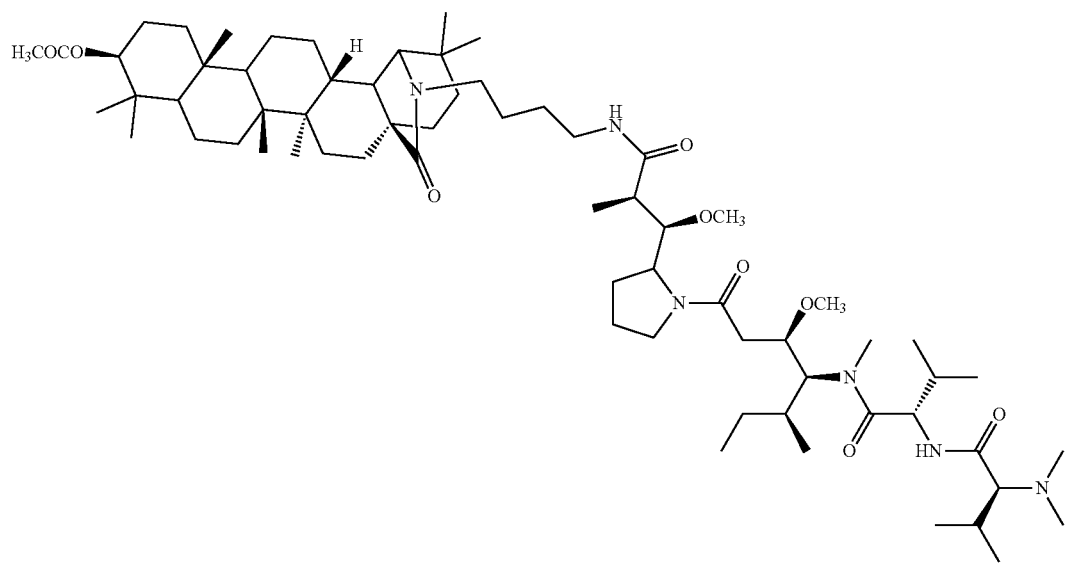

-continued

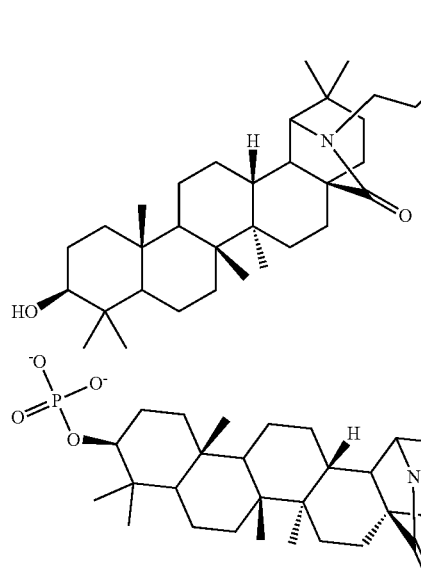
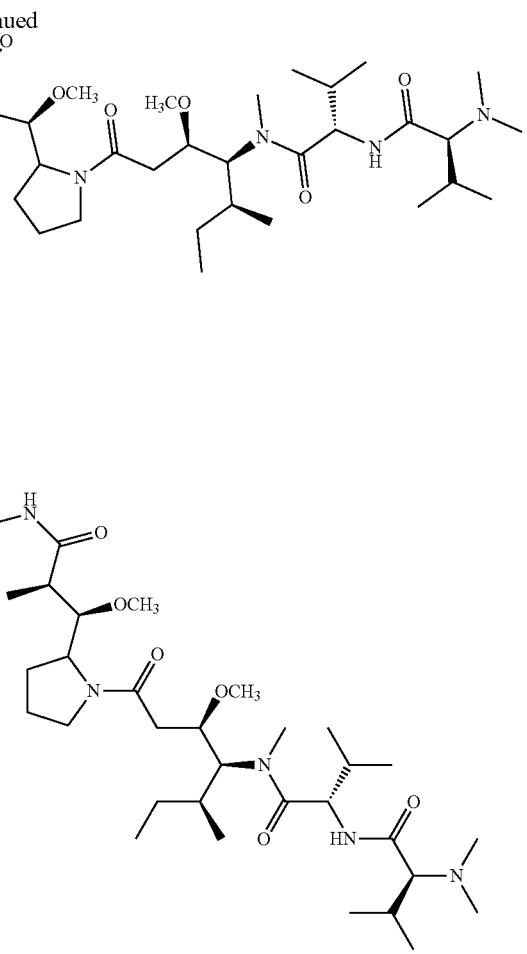

and pharmaceutically acceptable salts thereof.

Pharmaceutical Compositions

According to another embodiment, the present disclosure provides a pharmaceutical composition comprising a compound described herein or a pharmaceutically acceptable salt thereof and a pharmaceutically acceptable carrier.

The pharmaceutical composition of the disclosure may be formulated for administration in solid or liquid form, including those adapted for administration by oral, nasal, parenteral, rectal, topical, ocular, inhalation and intra-tumor administration. Parenteral administration includes subcutaneous injections, intravenous, intramuscular or intrasternal injection or infusion techniques. In one embodiment, the compositions are administered parenterally. In another embodiment, the compositions are administered intravenously.

The pharmaceutical composition of the disclosure may be in the form of a liquid, e.g., a solution, emulsion or suspension, pellets, powders, sustained-release formulations, or any other form suitable for use. The pharmaceutical composition may comprise sterile diluents such as water, saline solution, preferably physiological saline, Ringer's solution, isotonic sodium chloride, fixed oils such as synthetic mono- or digylcerides, which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates, phosphates or amino acids; agents for the adjustment of tonicity such as sodium chloride or dextrose; surfactants; preservatives; wetting agents; dispersing agents; suspending agents; stabilizers; solubilizing agents; local anesthetics, e.g., lignocaine; or isotonic agent.

It should be understood that a specific dosage and treatment regimen for any particular patient will depend upon a variety of factors, including the type of patient (e.g., human), the activity of the specific compound employed, the composition employed, the manner of administration, the age, body weight, general health, sex, diet, time of administration, rate of excretion, drug combination, and the judgment of the treating physician and the nature and the severity of the particular disorder being treated. The amount of active ingredients will also depend upon the particular compound in the composition. The amount of active ingredient can be determined by standard clinical techniques. In addition, in vitro or in vivo assays can optionally be employed to help identify optimal dosage ranges.

Preferably, the compositions are formulated so that a dosage of between about 0.01 to about 20 mg/kg body weight/day of the compound of formula (I) can be administered to a patient receiving the composition. In one embodiment, the dosage administered to the patient is between about 0.01 mg/kg and about 10 mg/kg of the patient's body weight. In another embodiment, the dosage administered to the patient is between about 0.1 mg/kg and about 10 mg/kg of the patient's body weight. In yet another embodiment, the dosage administered to the patient is between about 0.1 mg/kg and about 5 mg/kg of the patient's body weight. In yet another embodiment, the dosage administered is between about 0.1 mg/kg and about 3 mg/kg of the patient's body weight. In yet another embodiment, the dosage administered is between about 1 mg/kg and about 3 mg/kg of the patient's body weight.

The pharmaceutical compositions comprise an effective amount of a compound described herein such that a suitable dosage will be obtained. Typically, this amount is at least about 0.01% of a compound by weight of the composition. In a preferred embodiment, pharmaceutical compositions are prepared so that a parenteral dosage unit contains from about 0.01% to about 2% by weight of the compound of the disclosure.

For intravenous administration, the pharmaceutical composition may comprise from about 0.01 to about 100 mg of a compound described herein per kg of the patient's body weight. In one aspect, the composition may include from about 1 to about 100 mg of a compound described herein per kg of the patient's body weight. In another aspect, the amount administered will be in the range from about 0.1 to about 25 mg of a compound described herein per kg of body weight.

The pharmaceutical compositions of the disclosure may optionally further comprise a second therapeutic agent in a therapeutically effective amount. The second therapeutic agent includes those that are known and those discovered to be effective in treating cancer. In some embodiments, the second therapeutic agent may be selected from the group consisting of a tubulin-forming inhibitor, a topoisomerase inhibitor, and a DNA binder.

Methods of Use

According to another embodiment, the present disclosure provides methods of using the compounds described herein or pharmaceutical compositions thereof. The compounds and compositions are useful for killing or inhibiting the proliferation of tumor cells or cancer cells. The compounds and compositions are also useful for treating cancer in a patient.

In some embodiments, the present disclosure provides methods of killing or inhibiting the proliferation of tumor cells or cancer cells. In some embodiments, the method comprises contacting the tumor cells or cancer cells with a compound described herein, or a pharmaceutically acceptable salt thereof, in an amount effective to kill or inhibit the proliferation of the tumor cells or cancer cells. In alternate embodiments, the method comprises contacting the tumor cells or cancer cells with a pharmaceutical composition comprising a compound of formula (I) in an amount effective to kill or inhibit the proliferation of the tumor cells or cancer cells.

In some embodiments, the method further comprises contacting the cells with an effective amount of a second therapeutic agent or a pharmaceutical composition thereof. In one embodiment, the second therapeutic agent is selected from the group consisting of a tubulin-forming inhibitor, a topoisomerase inhibitor, and a DNA binder.

The cells may be contacted with the compound described herein and the second therapeutic agent simultaneously in either the same or different compositions or sequentially in any order. The amounts of compound described herein and the second therapeutic agent and the relative timings of their contact will be selected in order to achieve the desired combined effect.

In another embodiment, the present disclosure provides a method of determining inhibition of cellular proliferation by a compound described herein. The method comprises contacting cells in a cell culture medium with the compound described herein and measuring the cytotoxic activity of the compound, whereby proliferation of the cells is inhibited. In some embodiments, the method further comprises culturing the cells for a period from about 6 hours to about 5 days.

Suitable cell lines are known to those skilled in the art and include those used for evaluating other anti-cancer drugs. Such cell lines include, but are not limited to, BXPC-3 (pancreas); MCF-7 (breast); SF-268 (CNS); NCI-H460 (lung); KM20L2 (colon); DU-145 (prostate); 786-0, (renal cell carcinoma); Caki-1 (renal cell carcinoma); L428 (Hodgkin's disease); UMRC-3 (renal cell carcinoma); LP-1 (human myeloma); and U251 (glioblastoma). In some embodiments, the cells are obtained from a patient having a disease to be treated (e.g., cancer) or from a relevant cell line.

In another embodiment, the present disclosure provides a method of measuring cell viability in the presence of a compound described herein. The method comprises contacting cells in a cell culture medium with the compound of described herein, culturing the cells for a period from about 6 hours to about 5 days, preferably 96 hours; and measuring cell viability. In some embodiments, the cells are obtained from a patient having a disease to be treated (e.g., cancer) or from a relevant cell line.

In another embodiment, the present disclosure provides a method for treating cancer in a patient. In some embodiments, the method comprises administering to the patient a compound described herein, or a pharmaceutically acceptable salt thereof, in an amount effective to treat cancer. In other embodiments, the method comprises administering to the patient a composition comprising a compound described herein in an amount effective to treat cancer.

In some embodiments, the patient receives an additional treatment, such as radiation therapy, surgery, and chemotherapy with another chemotherapeutic agent or combinations thereof. In some embodiments, the compound of the disclosure is administered concurrently with the chemotherapeutic agent or with radiation therapy or with surgery. In other embodiments, the chemotherapeutic agent or radiation therapy or surgery is administered or performed prior or subsequent to administration of a compound of the disclosure.

In some embodiments, the method for treating cancer further comprises administering to the patient an effective amount of a second therapeutic agent, e.g., a chemotherapeutic agent. Any one or a combination of the chemotherapeutic agents, such a standard of care chemotherapeutic agent(s), can be administered. In some embodiments, the chemotherapeutic agent may be selected from the group consisting of a tubulin-forming inhibitor, a topoisomerase inhibitor, and a DNA binder.

The compound described herein and the chemotherapeutic agent may be administered simultaneously in either the same or different pharmaceutical composition or sequentially in any order. The amounts of compound described herein and the chemotherapeutic agent and the relative timings of their administration will be selected in order to achieve the desired combined effect.

Any compound or pharmaceutical composition described herein may be used in the methods of the present disclosure.

In some of the above methods, the compound described herein is administered to a patient in a composition comprising a pharmaceutically acceptable carrier. In some of these embodiments, the composition is administered intravenously. In certain embodiments, the compound is formulated in a unit dosage injectable form.

In preferred embodiments of each of the above methods, the patient is a human.

In an additional embodiment, the present disclosure provides the use of a compound of described herein in the manufacture of a medicament for the treatment of any of the above mentioned cancers. It will be appreciated that a compound described herein and one or more chemotherapeutic agents may be used in the manufacture of the medicament.

In additional embodiments, the present disclosure provides an article of manufacture comprising a compound described herein, a container, and a package insert or label indicating that the compound can be used to treat cancer characterized by the overexpression of at least one tumor-associated antigen.

The term "package insert" is used to refer to instructions customarily included in commercial packages of therapeutic products, that contain information about the indication(s), usage, dosage, administration, contraindications and/or warnings concerning the use of such therapeutic products.

In order that this invention be more fully understood, the following examples are set forth. These examples are for the purpose of illustration only and are not to be construed as limiting the scope of the invention in any way.

EXAMPLES

The compounds of this disclosure may be prepared by methods known to those skilled in the art, or the methods set forth below. By following the methods below, additional compounds of the disclosure can be prepared by modifying the choice of starting materials, reagents and reaction conditions as known to those skilled in the art.

General Experimental procedures. Both N-Boc-Dolaproine[10a] and Dov-Val-Dil.TFA[11] were synthesized as described earlier. Other reagents including diethyl cyanophosphonate (DEPC) and anhydrous solvents were purchased from Sigma-Aldrich Chemical Company and were used as received. Small quantities of betulin (1) were purchased from Sigma-Aldrich, and larger quantities were isolated[5] from white birch bark collected in the state of Maine by Professor Robert Dunlap, Department of Chemistry, University of Maine, and Mr. B. Deane as well as Hardwood Products Company LLC, Guilford, Maine.

Melting points are uncorrected and were determined with a Fisher Scientific melting point apparatus. Optical rotations were measured by use of a Rudolph Research Autopol IV automatic polarimeter. The $[\alpha]_D$ values are given in $10^{-1}$ deg cm$^2$ g$^{-1}$. The $^1$H, $^{13}$C spectra were recorded on Varian Unity INOVA 400 and 500 and Bruker 400 instruments with deuterated solvents. High resolution mass spectra were obtained employing a JOEL LCMate instrument and and a Bruker MicrOTOF-Q in ESI positive mode (direct infusion with internal calibration) in the Arizona State University CLAS High Resolution Mass Spectroscopy Laboratory. And we thank Dr John C. Knight and Natalya Zolotova for that very helpful data. For thin-layer chromatography, Analtech silica gel GHLF Uniplates were used and visualized with short-wave UV irradiation and an iodine chamber. For column chromatography, silica gel (230-400 mesh ASTM) from E. Merck (Darmstadt, Germany) was employed.

Example 1—Synthesis of Betulin-28-amino-N-(Dap-Dil-Val-Dov) (7b)

The synthesis of 7b was carried out as shown in Scheme 1.

Scheme 1.

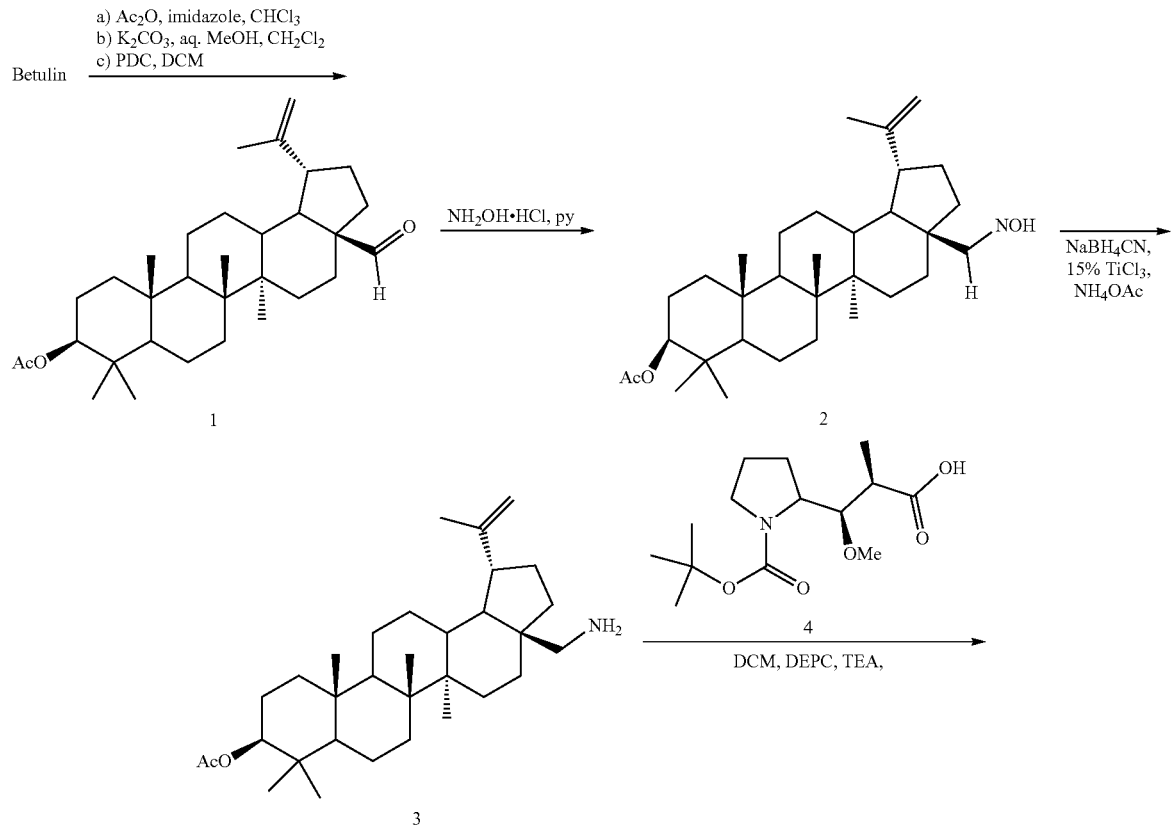

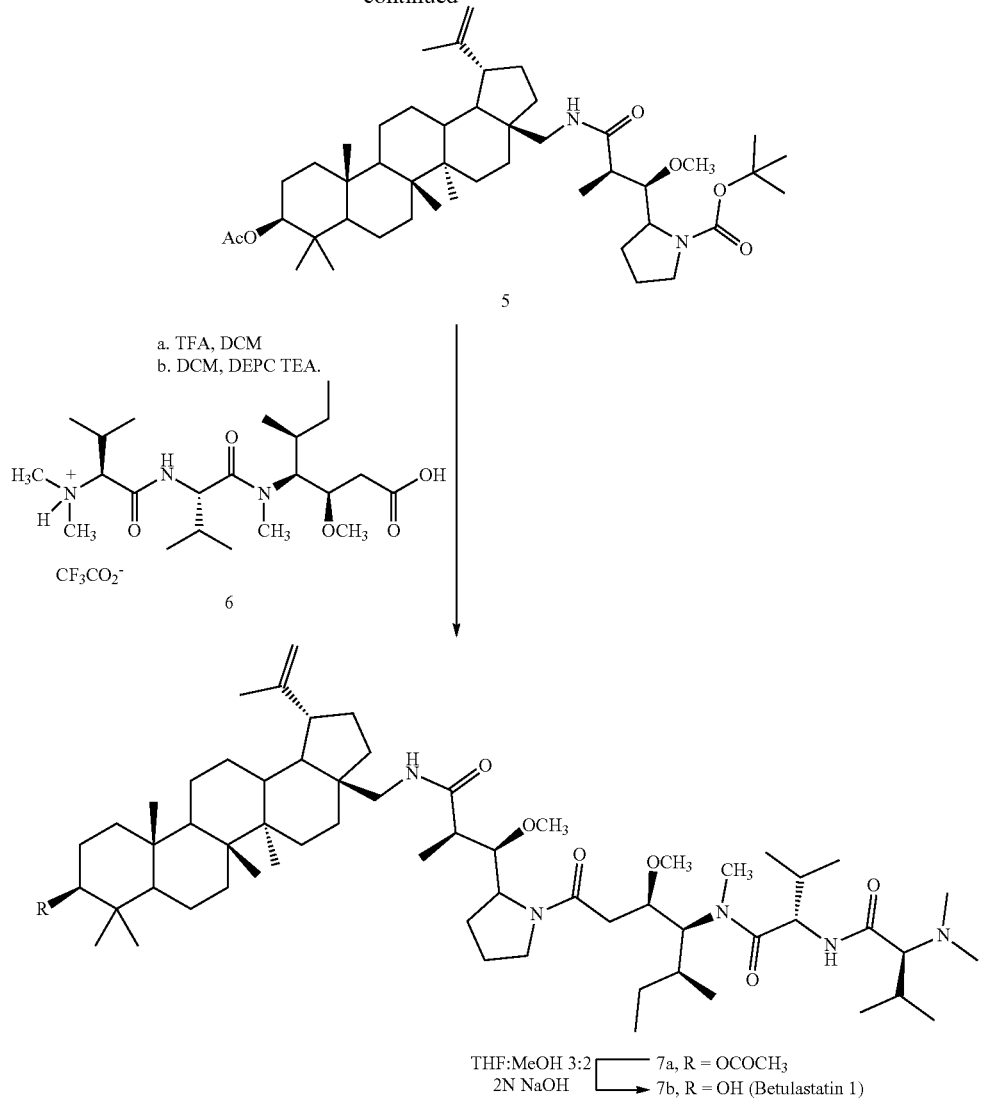

7a, R = OCOCH₃
7b, R = OH (Betulastatin 1)

3-O-Acetyl-28-betulinal (1). 3-O-acetylbetulin was prepared from the diacetate as described previously,[7a] and purified using column chromatography on silica gel eluting with hexanes-EtOAc 8:2). Recrystallization from CH$_2$Cl$_2$/MeOH yielded colorless plates: TLC R$_f$=0.7 (CH$_2$Cl$_2$: MeOH 98%:2%); mp 260-261° C.; [α]$^{20}_D$ +28.2 (c 0.7, CHCl$_3$), lit.[7a] mp 256-258° C.; lit.[7b] mp 258-260° C.; [α]$^{20}_D$ +26 (c 0.9, CHCl$_3$). $^1$H and $^{13}$C NMR spectroscopic data are in agreement with published data.[7a,c] 3-O-acetylbetulinal (1) was prepared as described[7b] from 3-O-acetylbetulin to yield a colorless crystalline solid; mp 170-175° C., [α]$^{20}_D$ +22 (c 0.6, CHCl$_3$) [lit.[7b] [α]$^{20}_D$ +32 (c 0.7, CHCl$_3$)]; $^1$H and $^{13}$C NMR data are in agreement with reported data.[7b]

3-O-Acetyl-28-oxime-betulin (2). 3-O-acetylbetulinal (1) (0.25 g, 0.5 mmol) was dissolved in dry pyridine (5 ml) and NH$_2$OH·HCl (0.1 g, 1.5 mmol, 3 equiv.) was added. The solution was heated at reflux for 2 h and monitored by tlc (hexanes-EtOAc 8:2). The reaction mixture was cooled and added to iced water (100 mL) and the resulting white precipitate filtered and dried under vacuum to yield oxime 2 (0.22 g, 86% yield). Crystallization of 2 from hot MeOH gave colorless crystals; mp 255-257° C.; lit[8] mp >260° C.

TLC R$_f$=0.5 (hexanes:EtOAc 8:2); $^1$H NMR (CDCl$_3$, 400 MHz) δ 8.12 (1H, s, NOH), 7.52 (1H, s, H-28), 4.69 (1H, bs, H-29), 4.58 (1H, s, H-29), 4.45 (1H, dd, J=10, 6 Hz, H-3), 2.49 (1H, dt, J=12, 6 Hz, H-19), 2.02 (3H, s, OCOCH$_3$), 1.68 (3H, s), 0.97 (3H, s), 0.95 (3H,), 0.82 (6H, s), 0.81 (3H, s); $^{13}$C NMR (CDCl$_3$, 100 MHz,) 171.1, 155.4, 149.7, 110.1, 80.9, 55.3, 50.3, 49.7, 49.3, 47.9, 42.8, 40.9, 38.6, 38.3, 37.7, 37.04, 37.02, 34.2, 32.3, 29.7, 27.9, 27.8, 25.1, 23.7, 21.3, 20.8, 19.1, 18.1, 16.5, 16.1, 16.0, 14.7; (+)-HRAPCIMS m/z 498.3953 (M+H)$^+$ (calcd for C$_{32}$H$_{52}$NO$_3$, 498.3947).

3-O-Acetyl-28-aminobetulin (3). To a stirred solution of 3-O-acetyl-28-oxime-betulin (2) (0.35 g, 0.7 mmol) in MeOH (50 mL) and cooled to 0° C. (ice-bath) was added NH$_4$OAc (0.75 g, 9.7 mmol, 14 equiv) and NaBH$_4$CN (0.6 g, 0.97 mmol). TiCl$_3$ (10 wt % in 20-30 wt % HCl) (3 mL) was then added dropwise to the cooled mixture. The reaction flask was removed from the cold bath after 2 h and the mixture stirred at rt for 1 h. Next 2N NaOH (20 mL) was added dropwise to the mixture until pH 10. MeOH was removed under vacuum and the aqueous suspension was extracted with CH$_2$Cl$_2$ (200 ml). The organic fraction was separated and washed with water until it was at neutral pH (3×30 ml), dried (Na$_2$SO$_4$), and concentrated to a solid (0.25 g, 71% yield): $^1$H NMR (CDCl$_3$, 400 MHz) δ 4.66 (1H, bs, H-29), 4.56 (1H, bs, H-29), 4.45 (1H, dd, J=10, 6 Hz, H-3), 2.85 (1H, d, J=13 Hz, H-28a), 2.35 (2H, m), 2.15 (1H, m), 2.02 (3H, s, OCOCH$_3$), 1.66, 1.00, 0.95, 0.83, 0.82, 0.81 (3H, s, 6×CH$_3$), 2.0-0.7 (CH, CH$_2$, NH$_2$); $^{13}$C NMR (CDCl$_3$, 100 MHz) 171.0, 150.6, 109.6, 80.9, 55.3, 50.3, 48.9, 47.4, 47.3, 42.6, 40.9, 39.2, 38.3, 37.8, 37.0, 36.9, 34.1, 34.0, 29.7, 29.3, 27.9, 27.0, 25.1, 23.7, 21.3, 20.9, 19.1, 18.2, 16.5, 16.1, 15.9, 14.7; (+) HRAPCIMS m/z 484.4147 (M+H)$^+$ (calcd for C$_{32}$H$_{54}$NO$_2$, 484.4155). The product was used immediately without further purification in the next reaction.

3-O-Acetyl-28-amino-N-(Boc-dap)-betulin (5). To a stirred solution of amine 3 (0.16 g, 0.33 mmol) in anhydrous CH$_2$Cl$_2$ (10 mL) at 0° C., Boc-Dap (4)$^{10}$ (0.08 g, 0.27 mmol) was added. The solution was cooled in an ice bath and TEA (0.16 mL, 3.5 equiv) followed by DEPC (0.1 mL, 0.62 mmol, 2 equiv) were added to the reaction mixture. Stirring with warming to rt was continued for 24 h. The mixture was then concentrated and purified using silica gel chromatography with gradient elution (100% hexane→hexanes-EtOAc 7:3) to give 5 (0.1 g, 46%) as a waxy solid. Crystallized from hexanes with cooling gave a colorless solid: mp 116-119° C., [α]$^{20}$$_D$ –11 (c 0.65, CHCl$_3$); $^1$H NMR (CDCl$_3$, 400 MHz) 6.39 (1H, bs), 5.57 (1H, bs), 4.68 (1H, s), 4.58 (1H, s), 4.46 (1H, dd, J=9.6, 6.4 Hz), 3.86-3.76 (2H, m) 3.55 (1H, m), 3.44 (3H, s, OCH$_3$), 3.39 (1H, m), 3.26 (1H, m) 3.13-3.02 (1H, m), 2.47 (2H, m, H-19, H-28), 2.03 (3H, s, OCOCH$_3$), 1.68, 1.05, 0.95 (3H, s, CH$_3$), 0.84 (2×CH$_3$) 0.83 (3H, s) 0.7-1.95 (CH, CH$_2$ hydrogens). $^{13}$C NMR (CDCl$_3$, 100 MHz) δ 174.6, 170.9 150.4, 109.4, 80.9, 60.8, 55.4, 50.3, 48.9, 47.3, 46.8, 44.5, 42.6, 40.9, 38.3, 37.8, 37.1, 37.0, 36.6, 34.9, 34.0, 30.3, 28.5, 27.9, 27.1, 25.9, 24.7, 23.7, 23.4, 21.3, 20.8, 19.2, 18.1, 16.5, 16.1, 16.09, 14.7; (+)-HRAPCIMS m/z 753.5776 (M+H)$^+$ (calcd for C$_{46}$H$_{77}$N$_2$O$_6$, 753.5782).

3-O-Acetyl-28-amino-N-(Dap-Dil-Val-Dov)-betulin (7a). 3-O-Acetyl-28-N-(Boc-Dap)-betulin (5) (0.07 g, 0.086 mmol) was dissolved in anhydrous CH$_2$Cl$_2$ (4 mL) and cooled in an ice-bath. TFA (1.5 mL) was added and the solution stirred for 1 h. The product mixture was then concentrated to remove the solvent and TFA was removed under reduced pressure to yield 3-O-acetyl-28-amino-N-(dap)-betulin TFA salt as a foamy solid. The salt was then stirred together with Dov-Val-Dil-TFA (6)$^{11}$ (0.045 g, 0.083 mmol) in anhydrous CH$_2$Cl$_2$ (5 mL) under N$_2$ at 0° C. TEA (0.06 mL, 0.42 mmol) and DEPC (0.02 mL, 0.15 mL, 1.8 equiv.) were added in succession and the reaction mixture stirred for 24 h with warming to rt, concentrated and purified on silica gel eluting with CH$_2$Cl$_2$:MeOH 95%: 5% to give 7a as an off-white solid (0.05 g, 45% yield). Attempts at crystallizing 7a from hexanes-acetone gave a fine powder: mp 129-131° C.; $^1$H NMR (CDCl$_3$, 400 MHz) δ 7.07 (1H, bs), 6.41 (1H, bs), 4.80-4.64 (2H, m), 4.53 (1H, s), 4.42 (1H, m), 4.12-4.02 (2H, m), 3.89 (1H, m), 3.42-2.99 (8H, m), 3.10-3.04 (1H, m), 2.98 (3H, s), 2.60-2.20 (11H, m), 2.08-1.92 (8H, m), 1.86-1.42 (16H, m), 1.40-1.14 (13H, m), 1.04-0.73 (40H, m). $^{13}$C NMR (CDCl$_3$, 100 MHz) 174.7, 173.5, 171.5, 171.2, 170.5, 150.5, 109.8, 82.2, 81.1, 78.3, 77.5, 61.5, 60.7, 59.7, 58.2, 55.5, 54.1, 50.5, 49.2, 48.8, 47.5, 47.2, 44.6, 42.8, 42.7, 41.1, 38.5, 37.9, 37.7, 37.4, 37.2, 35.2, 34.2, 33.4, 31.0, 30.5, 29.9, 28.1, 27.9, 27.3, 25.9, 25.3, 25.1, 25.08, 23.8, 21.5, 20.9, 20.2, 19.7, 19.5, 18.3, 18.1, 16.7, 16.3, 16.2, 16.0, 14.9, 14.87, 10.7; (+) HRFABMS m/z 1064.8355 (calcd. for C$_{63}$H$_{110}$N$_5$O$_8$ 1064.8354).

Betulin-28-amino-N-(Dap-Dil-Val-Dov) (7b). To a solution of acetate 7a (0.024 g, 0.022 mmol) in a mixture of THF-MeOH 3:2 (0.7 mL) was added aq. 2N NaOH (0.15 mL). The reaction mixture was stirred at rt for 24 h. Water (1 mL) was added and the mixture extracted into EtOAc (2×1 mL), the combined organics were concentrated and separated by flash silica gel column chromatography (CH$_2$Cl$_2$-MeOH 96%:4%) to yield a colorless solid, 12 mg (50% yield): mp 150° C.; $^1$H NMR (CDCl$_3$, 400 MHz) δ 6.88 (1H, d, J=8.8 Hz), 6.45 (1H, bs), 4.78 (1H, dd, J=8.4, 6.8 Hz), 4.68 (1H, s), 4.57 (1H, s), 4.12 (2H, m), 3.91 (1H, d, J=8 Hz), 4.38 (2H, m), 3.40, 3.32 (OCH$_3$, s), 3.41-3.26 (10H, m), 3.16 (2H, m), 3.10 (1H, s), 3.01 (3H, s), 2.48-2.29 (5H, m), 2.24 (6H, s), 2.11-1.95 (6H, m), 1.88-1.58 (12H, m), 1.46-1.32 (6H, m), 1.30-1.18 (8H, m), 1.13 (1H, d, J=8.6 Hz), 1.09-0.88 (27H, m,), 0.81 (6H, t, J=7.5 Hz), 0.75 (3H, s), 0.67 (1H, m); (+)HRAPCIMS m/z 1022.8246 [M+H]$^+$ (calcd. for C$_{61}$H$_{108}$N$_5$O$_7$, 1022.8250).

Example 2—Synthesis of 3β-Amino-N-(Dap-Dil-Val-Dov)-betulin (11b)

The synthesis of 11b was carried out as shown in Scheme 2.

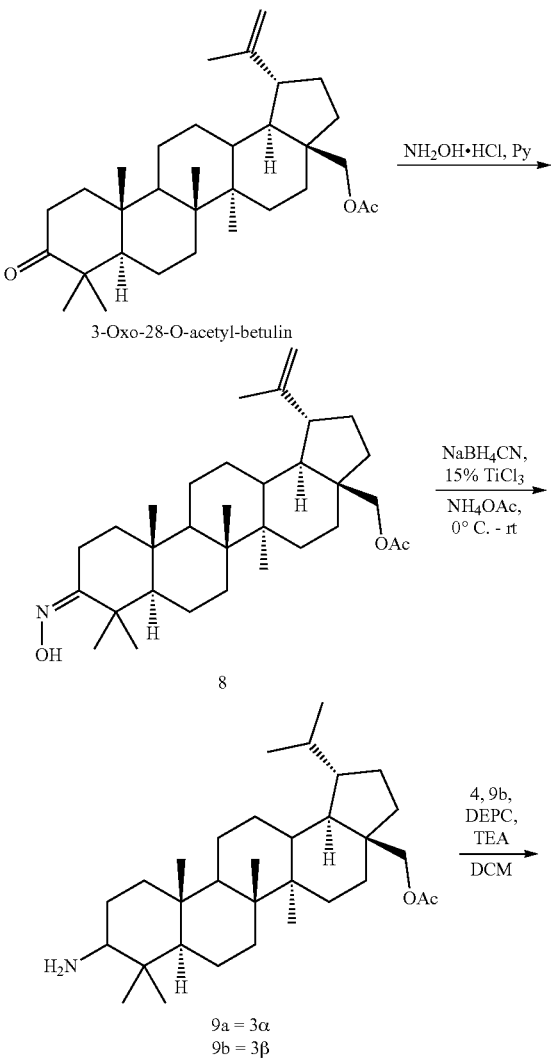

Scheme 2.

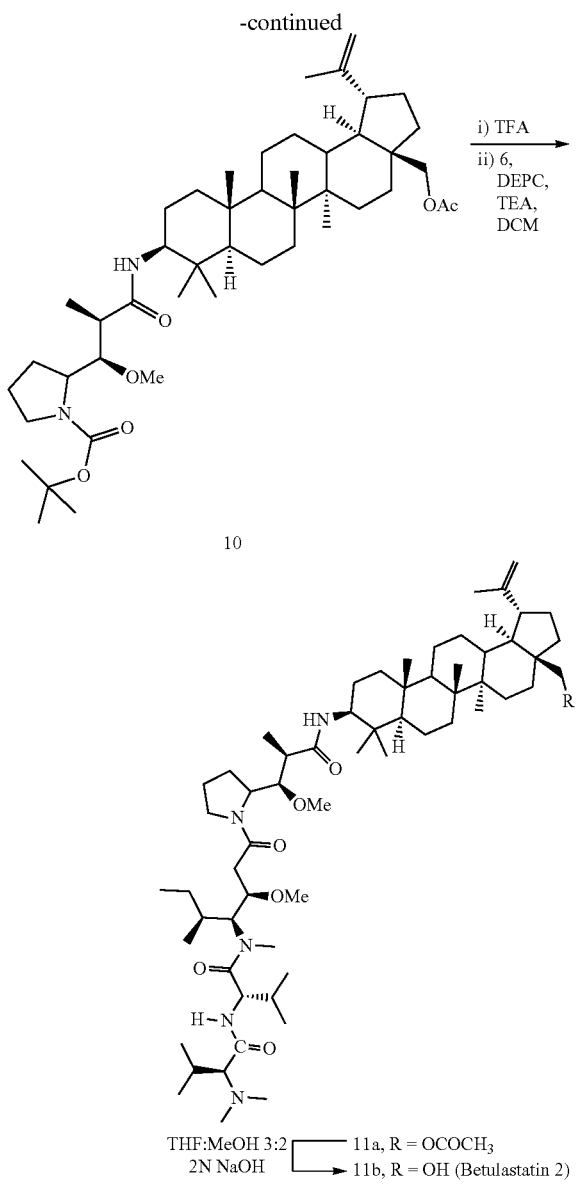

3-Oxime-28-O-acetyl-betulin (8). A solution of 3-Oxo-28-O-acetyl-betulin[12] (0.1 g, 0.21 mmol) and $NH_2OH \cdot HCl$ (0.06 g, 4 equiv) in anhydrous pyridine (5 mL) was heated at 80° C. for 2 h. The reaction was cooled to room temperature, diluted with $CH_2Cl_2$ (15 mL), and washed with 20% HCl (3×15 mL), brine (3×15 mL), dried over $Na_2SO_4$, filtered and the filtrate was concentrated under reduced pressure. The crude product was separated by chromatography on silica gel and eluting with 5:1 hexanes-EtOAc gave a colorless foamy solid (90 mg, 87%), which was crystallized from $CHCl_3$:MeOH; mp 205° C.; [lit.[12] mp 203-204° C.]; $R_f$ 0.4 (9:1 hexanes-EtOAc); $^1$H NMR ($CDCl_3$, 400 MHz) δ 9.17 (1H, s, OH), 4.66, 4.56 (1H each, s, H-29), 4.22, 3.83 (1H each, d, H-28), 2.96 (1H, dt, J=14, 4 Hz, H-2 eq), 2.42 (1H, m, H-19), 2.20 (1H, m), 2.04 (3H, s, $OCOCH_3$), 1.66, 1.11, 1.03, 1.02, 0.93, 0.90 (3H each, s, $CH_3$); $^{13}$C NMR: ($CDCl_3$, 100 MHz) δ 171.6, 167.0, 150.1, 109.9, 62.8, 55.5, 49.9, 48.7, 47.7, 46.3, 42.7, 40.9, 40.3, 38.8, 37.5, 37.2, 34.5, 33.8, 29.7, 29.5, 27.2, 27.0, 25.2, 22.9, 21.0, 19.1, 19.0, 17.1, 16.0, 15.8, 14.6; (+)-HRAPCIMS m/z 498.3949 [M+H]$^+$ (calcd. for $C_{32}H_{51}NO_3$, 498.3947).

3-α/β-Amino-28-O-acetyl-betulin (9a 9b). Oxime 8 (0.38 g, 0.76 mmol) was suspended in MeOH (50 mL) at rt, $NH_4OAc$ (0.88 g, 11.4 mmol, 15 equiv) and $NaBH_3CN$ (0.96 g, 15.2 mmol, 20 equiv) were added. Next $TiCl_3$ (15 wt % in 20-30 wt % HCl, 2.3 mL) was added in 0.1 mL aliquots over 45 min. The mixture was stirred at rt for 18 h, then 2N NaOH was added dropwise until pH 10. The mixture was concentrated under reduced pressure to an aqueous residue which was extracted with $CH_2Cl_2$ (2×100 mL). The combined organic extract was washed with $H_2O$ until neutral pH, dried ($Na_2SO_4$), and concentrated under reduced pressure to a colorless solid (0.3 g, 80% yield). After separation by column chromatography eluting with $CH_2Cl_2$:MeOH:$NH_4OH$ 95:4:1 3α amine (9a) was obtained as a colorless glassy solid (0.065 g, 18% yield): TLC $R_f$ 0.2 ($CH_2Cl_2$:MeOH:$NH_4OH$ 95:4:1); mp 80-85° C.; $[\alpha]^{23}_D$ +0.31 (c 1.9, $CHCl_3$); $^1$H NMR ($CDCl_3$, 400 MHz) δ 4.66 (1H, s), 4.56 (1H, s), 4.22 (1H, d, J=12 Hz), 3.83 (1H, d, J=12 Hz), 2.56 (1H, nm, H-3β) 2.42 (1H, td, J=11, 6 Hz), 2.05 (3H, s, $OCOCH_3$), 2.0-1.88 (2H, m), 1.82 (1H, ddd, J=10, 2, 4 Hz), 1.74 (1H, dd, J=12, 8 Hz), 1.20-0.80 (22H, m, $CH_2$, CH ring protons), 1.66, 1.00, 0.97, 0.85, 0.83, 0.81 (18H, s, $CH_3$); $^{13}$C NMR (100 MHz, $CDCl_3$) 171.9, 150.4, 110.0, 63.1, 56.7, 50.6, 49.0, 48.98, 47.9, 46.5, 43.0, 41.3, 37.7, 37.7, 34.8, 34.3, 33.6, 30.0, 29.8, 29.0, 27.2, 25.9, 25.4, 23.6, 21.3, 20.9, 19.3, 18.5, 16.3, 16.2, 15.1; (+)-HRAPCIMS m/z 484.4156 [M+H]$^+$ (calcd. for $C_{32}H_{54}NO_2$, 484.4155); And 3β amine (9b) as a colorless crystalline solid (0.24 g, 65%); TLC $R_f$ 0.13 ($CH_2Cl_2$:MeOH:$NH_4OH$, 95:4:1); mp 185° C.; $[\alpha]^{23}_D$ +3.4 (c 2.8, $CH_2Cl_2$); $^1$H NMR ($CDCl_3$, 400 MHz) δ 4.66 (1H, s), 4.56 (1H, s), 4.22 (1H, d, J=12 Hz), 3.83 (1H, d, J=12 Hz), 2.42 (1H, td, J=11, 6 Hz), 2.26 (1H, m, H-3α), 2.04 (3H, s, $OCOCH_3$), 2.00-1.86 (2H, m), 1.81 (1H, ddd, J=10, 4, 2 Hz) 1.74 (1H, dd, J=12, 8 Hz)), 1.70-0.60 (22H, m, $CH_2$, CH ring protons), 1.65, 1.00, 0.95, 0.89, 0.77, 0.67 (18H, s, $CH_3$); $^{13}$C NMR ($CDCl_3$, 100 MHz) δ 171.8, 150.3, 110.0, 63.0, 59.8, 56.1, 50.6, 49.0, 47.9, 46.5, 42.9, 41.0, 39.6, 37.8, 37.5, 34.7, 34.4, 30.0, 29.8, 28.5, 27.2, 25.4, 21.3, 20.9, 19.3, 18.9, 16.2, 15.6, 15.0; (+)-HRAPCIMS m/z 484.4150 (calcd for $C_{32}H_{54}NO_2$, 484.4155).

3-β-Amino-N-(Boc-Dap)-28-O-acetyl-betulin (10). Boc-Dap[10] (0.03 g, 0.10 mmol) was dissolved in dry $CH_2Cl_2$ (1 mL) and added to a solution of 9b (0.05 g, 0.01 mmol) in dry $CH_2Cl_2$ (3 mL), the solution was cooled to 0° C. (ice-bath), TEA (80 μL, 3.5 equiv)) followed by DEPC (0.025 mL, 0.16 mmol, 1.6 equiv) were then added. The solution was stirred for 18 h with warming to rt over time, and concentrated to an amber oil. The crude product was separated by column chromatography on silica gel eluting with hexanes:EtOAc 3:7 to yield a colorless oil, which crystallized from $CHCl_3$-hexanes (0.042 g, 56% yield): TLC $R_f$ 0.3 (hexanes:EtOAc 2:8); mp 105° C., $[\alpha]^{22}_D$ −7.1 (c 1.3, $CHCl_3$); $^1$H NMR ($CDCl_3$, 400 MHz) δ 5.83 (0.5H, bs, NH), 5.51 (0.5H, bs, NH), 4.65 (1H, s), 4.56 (1H, s), 4.22 (1H, d, J=11 Hz), 3.98-3.74 (3H, m), 3.62-3.48 (2H, m), 3.41 (3H, s, $OCH_3$), 3.20 (1H, m), 2.41 (1H, m), 2.27 (1H, m), 2.04 (2H, s, $OCOCH_3$), 1.99-0.70 (34H, m), 1.65, 0.99, 0.94, 0.83, 0.78, 0.72 (21H, 6s, $CH_3$); $^{13}$C NMR ($CDCl_3$, 100 MHz) (two conformers observed)[10c] δ 173.7, 173.2, 171.8, 154.7, 154.5, 150.2, 110.0, 84.1, 82.3, 79.9, 79.3, 62.9, 60.9, 60.5, 59.0, 56.5, 56.2, 56.1, 50.4, 48.9, 47.8, 47.1, 46.6, 46.4, 44.5, 43.9, 42.8, 40.9, 39.2, 37.9, 37.7, 37.1, 34.7, 34.2, 29.8, 29.7, 28.8, 27.2, 26.3, 25.7, 25.5, 25.3, 24.9, 24.7, 24.3, 21.2, 20.8, 19.2, 18.7, 16.6, 16.1, 14.8, 14.6, 14.3; (+)-HRAPCIMS m/z 753.5768 [M+H]$^+$ (calcd for $C_{46}H_{77}N_2O_6$, 753.5782)

3β-Amino-N-(Dap-Dil-Val-Dov)-28-O-acetyl-betulin (11a). Amide 10 (0.05 g, 0.067 mmol) was dissolved in anhydrous CH$_2$Cl$_2$ (1 mL) and cooled in an ice-bath. TFA (0.1 mL, 0.149 g. 1.3 mmol, 19 equiv) was added and the solution stirred for 3 h. Excess TFA was removed under reduced pressure for 2 h to yield a foamy solid. The TFA salt (0.43 g, 0.07 mmol) was stirred together with Dov-Val-Dil-TFA[11] (0.038 g, 0.07 mmol) in anhydrous CH$_2$Cl$_2$ (2 mL) under N$_2$ at 0° C. TEA (0.05 mL, 0.36 mmol, 15 equiv) and DEPC (0.011 mL, 0.71 mmol, 10 equiv) were then added. The reaction mixture was stirred for 18 h at rt, then concentrated and separated using column chromatography eluting with CH$_2$Cl$_2$:MeOH 97%:3% to give 11a as a colorless frothy solid (0.052 g, 74% yield). Further purification on sephadex LH-20 eluting with methanol gave a colorless crystalline solid, mp 135° C.; TLC R$_f$ 0.3 (CH$_2$Cl$_2$:MeOH 95%:5%); $^1$H NMR (CDCl$_3$, 500 MHz) two conformers were present and some signals were doubled δ 6.90 (1H, d, J=9.0 Hz), 5.92 (1H, dd, J=9.5, 4.5 Hz), 4.87 (1H, m), 4.79 (1H, dd, J=9.2, 6.6 Hz), 4.68 (1H, nm), 4.59 (1H, nm), 4.27-4.09 (3H, m), 4.02 (1H, d, J=6.8 Hz), 3.96 (1H, m), 3.88-3.74 (2H, m), 3.71-3.50 (2H, m), 3.49-3.36 (7H, m), 3.41 (s, OCH$_3$), 3.33 (4H, m), 3.32 (s, OCH$_3$), 3.15 (1H, s), 3.02 (3H, s), 2.51-2.37 (4H, m), 2.25 (9H, s), 2.07 (3H, s, OCOCH$_3$), 2.15-0.72 (CH, CH$_2$ and CH$_3$ protons betulin ring and peptide protons). $^{13}$C NMR (CDCl$_3$, 100 MHz) δ 173.6, 173.56, 171.9, 171.8, 170.2, 150.32, 110.0, 88.11, 86.3, 82.3, 78.2, 76.6, 62.9, 61.8, 60.4, 59.3, 58.1, 56.6, 56.2, 53.9, 51.1, 50.4, 48.9, 47.9, 47.8, 46.9, 46.8, 46.4, 45.5, 45.0, 43.8, 43.0, 42.9, 42.8, 41.6, 41.2, 41.0, 40.9, 40.7, 39.3, 38.0, 37.9, 37.7, 37.3, 37.2, 36.8, 36.4, 33.8, 31.9, 31.1, 29.9, 29.7, 28.9, 28.6, 27.8, 27.2, 26.6, 26.5, 26.0, 25.9, 25.5, 25.3, 25.1, 24.7, 23.7, 21.2, 20.9, 20.3, 19.9, 19.8, 19.2, 18.7, 17.9, 16.7, 16.6, 16.2, 15.9, 14.9, 14.1, 13.7, 11.0. (+)-HRAPCIMS m/z 1064.8360 (calcd for C$_{63}$H$_{110}$N$_5$O$_8$, 1064.8350).

3β-Amino-N-(Dap-Dil-Val-Dov)-betulin (Jib). A solution of 11a (0.042 g, 0.04 mmol) in THF:MeOH (0.8 mL:0.6 mL) was treated with 2N NaOH (0.3 mL) as described in the procedure for synthesis of 7b. Following separation of the reaction mixture by chromatography on a silica gel column (gradient elution CH$_2$Cl$_2$:MeOH 97%:3%→94%-4%) and drying, 11b was obtained as an amorphous powder (0.008 g, 19% yield); TLC R$_f$ 0.23 (CH$_2$Cl$_2$:MeOH 96%:4%); $^1$H NMR (CDCl$_3$, 500 MHz) 6.88 (1H, d, J=8.6 Hz), 5.91 (1H, d, J=9.6 Hz), 4.86-4.72 (2H, m), 4.68 (1H, s), 4.58 (1H, s), 4.23-4.10 (2H, m), 4.02 (1H, m), 3.80 (1H, d, J=10.8 Hz), 3.67-3.50 (2H, m), 3.50-3.30 (9H, m), 3.40 (s, OCH$_3$), 3.32 (s, OCH$_3$), 3.14 (s, 1H), 3.01 (s, 2H), 2.51-2.31 (5H, m), 2.28-2.22 (6H, nm), 2.25 (s, N(CH$_3$)$_2$, 2.13-0.74 (CH, CH$_2$, and CH$_3$ betulin ring and peptide protons, m); (+)-HRAPCIMS m/z 1022.8243 (calcd for C$_{61}$H$_{108}$N$_5$O$_7$, 1022.8250).

Example 3—Synthesis of 30-N-(Dap-Dil-Val-Dov)-betulin (16b)

The synthesis of 16b was carried out as shown in Scheme 3.

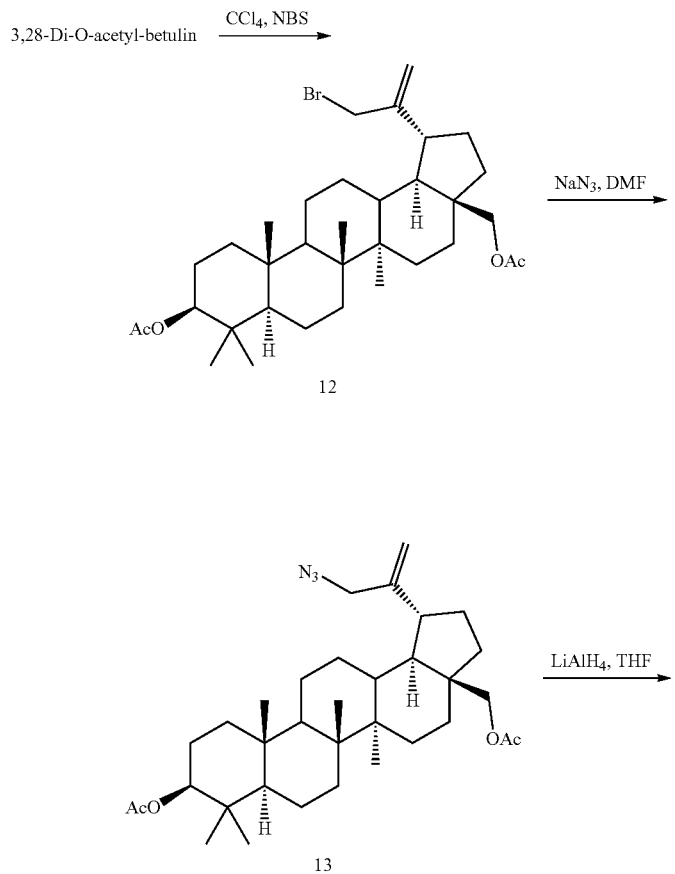

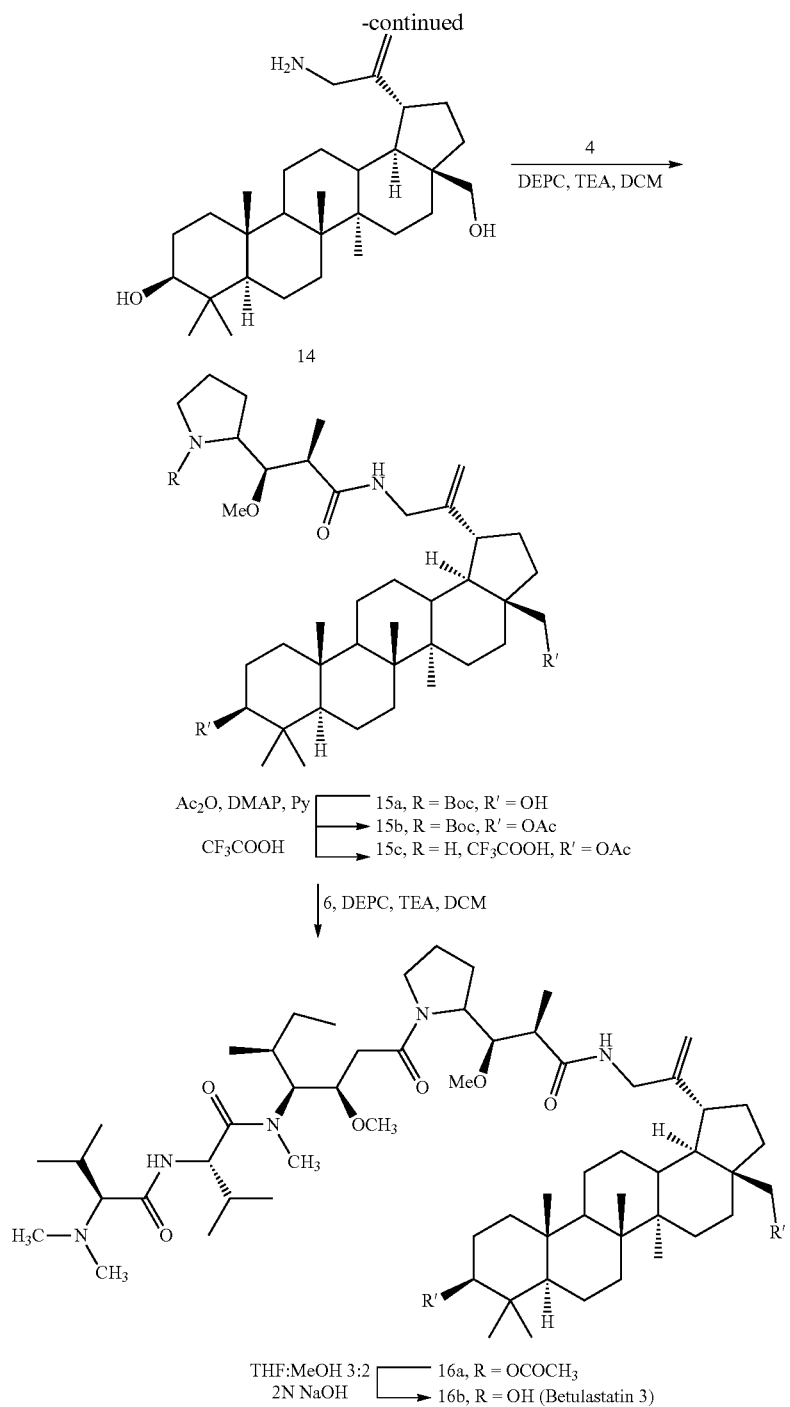

3,28-Di-O-acetyl-30-bromo-betulin (12). The bromination of diacetoxy betulin was carried out according to the literature.[13] Diacetoxybetulin (0.5 g, 0.8 mmol) was dissolved in dry $CCl_4$ (10 mL) and NBS (0.3 g, 1.7 mmol) was added, the reaction mixture was heated at reflux for 1.5 h. The precipitated solid was collected and crystallized from ethanol to give a colorless solid, 0.35 g (61%); mp 189-190° C., TLC $R_f$ 0.43 (hexanes:EtOAc 8:2). $^1H$ and $^{13}C$ NMR spectroscopic data were in accord with published data.

3,28-Di-O-acetyl-30-azido-betulin (13). To a solution of bromo-betulin 12 (1.25 g, 2.0 mmol) in anhydrous DMF (28 mL) was added $NaN_3$ (0.60 g, 9.2 mmol, 4.5 equiv) and the reaction mixture heated to 90° C. for 30 min, cooled and EtOAc (40 mL) was added followed by water (40 mL). The organic layer was extracted and washed with brine (2×40 mL), dried ($MgSO_4$) and concentrated to an off-white residue, crystallization from EtOAc gave azide 13 as a colorless solid (0.82 g, 70%); mp 185° C. [Lit[14] 192-193° C.]; TLC $R_f$ 0.5 (EtOAc:Hexanes 2:8); $^1H$ and $^{13}C$ NMR spectroscopic data were consistent with published data.[14] (+)-HRAPCIMS m/z 540.4052 (M+H-$N_2$)$^+$ (calcd for $C_{34}H_{54}NO_4$, 540.4053).

30-Amino-betulin (14). To a cooled (icebath) solution of azide 13 (0.1 g, 0.18 mmol) in dry THF (2.5 mL) was added LiAlH$_4$ (1 M in THF, 0.75 mL, 0.75 mmol, 4 equiv). The reaction mixture was stirred with warming to rt for 2 h, cooled and water (0.03 mL), 15% NaOH (0.03 mL) and water (0.09 mL) were added successively. The resulting mixture was stirred for 20 min before extraction with ether (25 mL). Anhydrous sodium sulfate was added and the mixture was allowed to stand overnight, filtered and concentrated to yield 14 as an off white solid, (68 mg, 85% yield) which was recrystallized from CHCl$_3$—CH$_3$OH: mp 210-215° C.; [α]$^{22}_D$ −2.1 (c 0.52, CH$_3$CH$_2$OH); TLC R$_f$ 0.1 (CH$_2$Cl$_2$—CH$_3$OH 10%); $^1$H NMR (CDCl$_3$, 400 MHz, sparingly soluble) δ 4.83 (2H, s), 3.77 (1H, d, J=11 Hz), 3.69 (1H, m), 3.30 (1H, d, J=11 Hz), 3.25 (1H, d, J=7.4 Hz), 3.21-3.14 (1H, m), 2.32-2.21 (1H, m), 2.13-2.00 (2H, m), 1.95-1.81 (4H, m), 1.73-1.01 (21H, CH$_2$, CH ring protons), 1.00, 0.96, 0.95, 0.80, 0.74 (15H, 5s, CH$_3$), 0.66 (1H, d, J=9 Hz); $^{13}$C-NMR (CD$_3$OD, 100 MHz) 156.7, 106.6, 79.6, 62.8, 60.1, 56.7, 51.5, 50.6, 48.9, 43.8, 42.1, 39.9, 38.6, 38.3, 35.5, 35.0, 30.9, 30.4, 30.1, 28.6, 28.2, 28.0, 27.8, 22.1, 19.4, 16.7, 16.6, 16.2, 15.2; (+)-HRAPCI m/z 458.3998 (M+H)$^+$ (calcd. for C$_{30}$H$_{52}$NO$_2$, 458.3998).

30-N-(Boc-dap)-betulin (15a). To a cooled (icebath) solution of amine 14 (0.15 g, 0.33 mmol) in dry CH$_2$Cl$_2$ (10 mL) was added a solution of Boc-Dap$^{10}$ (0.09 g, 0.30 mmol) in DCM (3 mL). TEA (0.24 mL, 1.71 mmol) and DEPC (0.033 mL, 2.13 mmol) were added and the reaction mixture was stirred for 20 h before terminating with removal of the solvent under low pressure overnight. Separation by flash silica gel chromatography (eluent: CH$_2$Cl$_2$:CH$_3$OH 98:2) gave amide 15a as a frothy solid (85 mg, 50% yield): TLC R$_f$ 0.2 (CH$_2$Cl$_2$—CH$_3$OH 96:4); mp 129-131° C.; $^1$H NMR (CDCl$_3$, 400 MHz) δ 6.56 (0.5H, bs), 5.84 (0.5H, bs), 4.81 (1H, s), 4.72 (1H, s), 3.93-3.64 (5H, m), 3.59-3.31 (1H, m), 3.40 (3H, s, OCH$_3$), 3.29-3.08 (3H, m), 2.45-2.19 (2H, m), 2.12-1.97 (1H, m), 1.96-0.67 (CH, CH$_2$ ring protons and Boc-Dap protons), 0.97, 0.93, 0.78, 0.73 (15H, 4s, CH$_3$), 0.65 (1H, m); $^{13}$C NMR (CDCl$_3$, 100 MHz) two conformers present; 174.2, 173.7, 154.9, 154.6, 151.7, 107.9, 84.2, 82.4, 80.9, 79.5, 79.0, 60.9, 60.3, 59.4, 58.8, 55.4, 50.5, 49.5, 47.9, 47.2, 46.7, 44.7, 44.2, 42.8, 41.1, 39.0, 38.9, 37.4, 37.3, 34.4, 34.0, 29.4, 28.7(m), 28.2, 27.5, 27.2, 26.2, 25.6, 24.8, 24.4, 21.1, 18.4, 16.3, 16.1, 15.6, 14.9; (+)-HRAPCI m/z 727.5631 (M+H)$^+$ (calcd. for C$_{44}$H$_{75}$N$_2$O$_6$, 727.5625).

30-N-(Boc-dap)-3, 28-di-O-acetoxy-betulin (15b). Alcohol 15a (0.08 g, 0.11 mmol) was taken up in dry pyridine (2 mL). Acetic anhydride (0.05 mL, 0.5 mmol) and DMAP (1 mg, 0.008 mmol) were added and the reaction mixture stirred at rt under N$_2$ for 24 h. Then CH$_2$Cl$_2$ (10 mL) was added and the organic fraction washed with cold 3N H$_2$SO$_4$ (4 mL), saturated NaHCO$_3$ (5 mL), brine (7 mL), dried (MgSO$_4$) and concentrated. Column chromatography (CH$_2$Cl$_2$-MeOH 98:2→86:4) on silica gel provided 15b as an off-white frothy solid (78 mg, 87% yield), TLC R$_f$ 0.5 (CH$_2$Cl$_2$:CH$_3$OH 96:4); mp 98-100° C.; $^1$H NMR (CDCl$_3$, 400 MHz) δ 6.28 (0.5H, bs), 5.81 (0.5H, bs), 4.82 (1H, nm), 4.73 (1H, m), 4.42 (1H, m), 4.20 (1H, d, J=12 Hz), 3.92-3.70 (5H, m), 3.56-3.27 (4H, m) 3.39 (s, OCH$_3$) 3.19 (1H, m), 2.48-2.25 (2H, m), 2.01 (3H, s, OCOCH$_3$), 1.99 (3H, s, OCOCH$_3$), 2.00 (1H, m), 1.93-1.50 (12H, m), 1.50-1.30 (16H, m), 1.43, 1.49 (s, Boc-CH$_3$), 1.28-1.00 (8H, m), 1.00-0.75 (16H, m), 0.98, 0.91, 0.79 (×2), 0.78 (s, CH$_3$), 0.73 (1H, m); $^{13}$C NMR (CDCl$_3$, 100 MHz) doubling of signals observed for the peptide portion of the molecule δ 174.1, 173.6, 171.65, 171.12, 155.0, 154.6, 151.3, 108.5, 84.4, 82.6, 81.0, 79.4, 62.6, 60.8, 59.3, 58.8, 55.5, 50.4, 49.6, 47.1, 46.7, 46.5, 45.1, 44.2, 42.8, 42.3, 41.1, 38.5, 37.9, 34.6, 34.3, 31.2, 29.9, 28.7, 28.1, 27.2, 26.6, 26.2, 25.6, 24.8, 24.4, 23.8, 21.4, 21.1, 21.0, 16.6, 16.3, 16.2, 14.5×2; (+)-HRESIMS m/z 811.5813 (M+H)$^+$ (calcd for C$_{48}$H$_{78}$N$_2$O$_8$, 811.5831).

30-N-(Dap)-3, 28-di-o-acetoxy-betulin trifluoroacetate (15c). TFA (0.15 mL, 0.22 g, 1.96 mmol) was added to a cooled solution of 15b (0.78 g, 0.096 mmol) in dry CH$_2$Cl$_2$ (1.5 mL) and stirring was continued with warming to rt under N$_2$ for 4 h. The product mixture was concentrated in the presence of toluene to aid in TFA removal and followed by further drying overnight under low pressure to give crude 15c as a frothy orange residue; TLC R$_f$ 0.2 (CH$_2$Cl$_2$-MeOH 92:8). The salt was used in the next step without further purification. 30-N-(Dap-Dil-Val-Dov)-3,28-di-O-acetoxy-betulin (16a). Dov-Val Dil-TFA salt (0.055 g, 0.10 mmol) was added to a solution of amide 15c (0.096 mmol) in dry DCM (2 mL) at rt. The reaction mixture was cooled in an ice bath and TEA (0.2 mL) and DEPC (0.17 mL, 0.18 g, 1.1 mmol) were added. Stirring was continued for 24 h with warming to rt overtime. The solvent was removed under vacuum to yield a brown residue. Separation by column chromatography on flash silica gel (eluent: CH$_2$Cl$_2$-MeOH 96:4) gave 16a as an off-white solid (50 mg). Further purification on a sephadex column LH-20 gave a frothy off-white solid (38 mg, 35% yield). TLC R$_f$ 0.5 (CH$_2$Cl$_2$-MeOH 96:4); $^1$H NMR (CDCl$_3$, 400 MHz) δ 6.90 (1H, d, J=9 Hz), 6.37 (1H, m), 4.90-4.74 (3H, m), 4.47 (1H, dd, J=11, 5.4 Hz), 4.25 (1H, d, J=10.8 Hz), 4.20-4.09 (2H, m), 3.97 (1H, dd, J=7.6, 2.3 Hz), 3.83 (2H, m), 3.80 (1H, d, J=10.8), 3.54-3.40 (2H, m), 3.42 (3H, s, OCH$_3$), 3.32 (3H, s, OCH$_3$), 3.03 (3H, s, NCH$_3$), 2.53-2.29 (5H, m), 2.25 (6H, s), 2.13-1.96 (11H, m), 1.88-1.74 (4H, m), 1.73-1.56 (7H, m), 1.54-1.32 (9H, m), 1.32-1.23 (5H, m), 1.20-1.05 (3H, m), 1.04-0.91 (24H, m), 0.88-0.74 (13H, m); $^{13}$C (CDCl$_3$, 100 MHz) δ 174.0, 173.6, 171.9, 171.7, 171.2, 170.5, 151.4, 108.2, 86.2, 82.4, 81.0, 78.5, 77.4, 76.7, 62.7, 60.6, 59.4, 58.1, 55.5, 53.9, 50.4, 49.5, 47.9, 46.5, 44.9, 44.3, 43.1, 42.8, 41.1, 38.6, 38.0, 37.8, 37.7, 37.2, 34.6, 34.3, 33.3, 31.2, 31.1, 29.9, 28.1, 27.8, 27.2, 26.6, 25.9, 25.2, 25.1, 23.9, 23.7, 21.5, 21.2, 21.1, 20.9, 20.3, 20.0, 19.7, 18.3, 17.9, 16.7, 16.3, 16.2, 16.0, 15.0, 14.5, 10.9; (+)-HRESIMS m/z 1122.8411 (M+H)$^+$ (calcd for C$_{65}$H$_{112}$N$_5$O$_{10}$, 1122.8404).

30-N-(Dap-Dil-Val-Dov)-betulin (16b). To a solution of 30-N-(Dap-Dil-Val-Dov)-3,28-di-O-acetoxy-betulin (16a) (0.02 g, 0.018 mmol) in a mixture of THF:MeOH (1.4 mL, 0.8:0.6), 2N NaOH (0.3 mL) was added. The solution was stirred at rt for 24 h. The solvent was evaporated and the residue separated on a silica gel column eluting with CH$_2$Cl$_2$:CH$_3$OH 95%:5% to give the product as a colorless solid, 0.013 g (70% yield): mp 145° C.; TLC R$_f$ 0.3 (DCM: MeOH 92%:8%). $^1$H NMR (CDCl$_3$, 500 MHz) δ 6.98-6.85 (1H, m), 6.42 (1H, m), 4.93-4.72 (3H, m), 4.15 (2H, m), 3.96 (1H, m), 3.90-3.65 (3H, m), 3.51-3.29 (7H, m), 3.42 (s, OCH$_3$), 3.33 (s, OCH$_3$), 3.19 (1H, m), 3.10, 3.03 (3H, s, NCH$_3$), 2.59-2.39 (3H, m), 2.33 (1H, m), 2.39-2.20 (7H, m), 2.25 (s, N(CH$_3$)$_2$), 2.15-0.74 (CH, CH$_2$ and CH$_3$ protons), 0.68 (1H, d, J=10.1 Hz). (+)-HRESIMS m/z 1038.8202 (M+H)$^+$ (calcd for C$_{61}$H$_{108}$N$_5$O$_8$, 1038.8192);

Example 4—Synthesis of 28-Amido-allobetulin-28-N-1'-ethyldiamine-N-2'-Dap-Dil-Val-Dov (18b)

The synthesis of 18b was carried out as shown in Scheme 4.

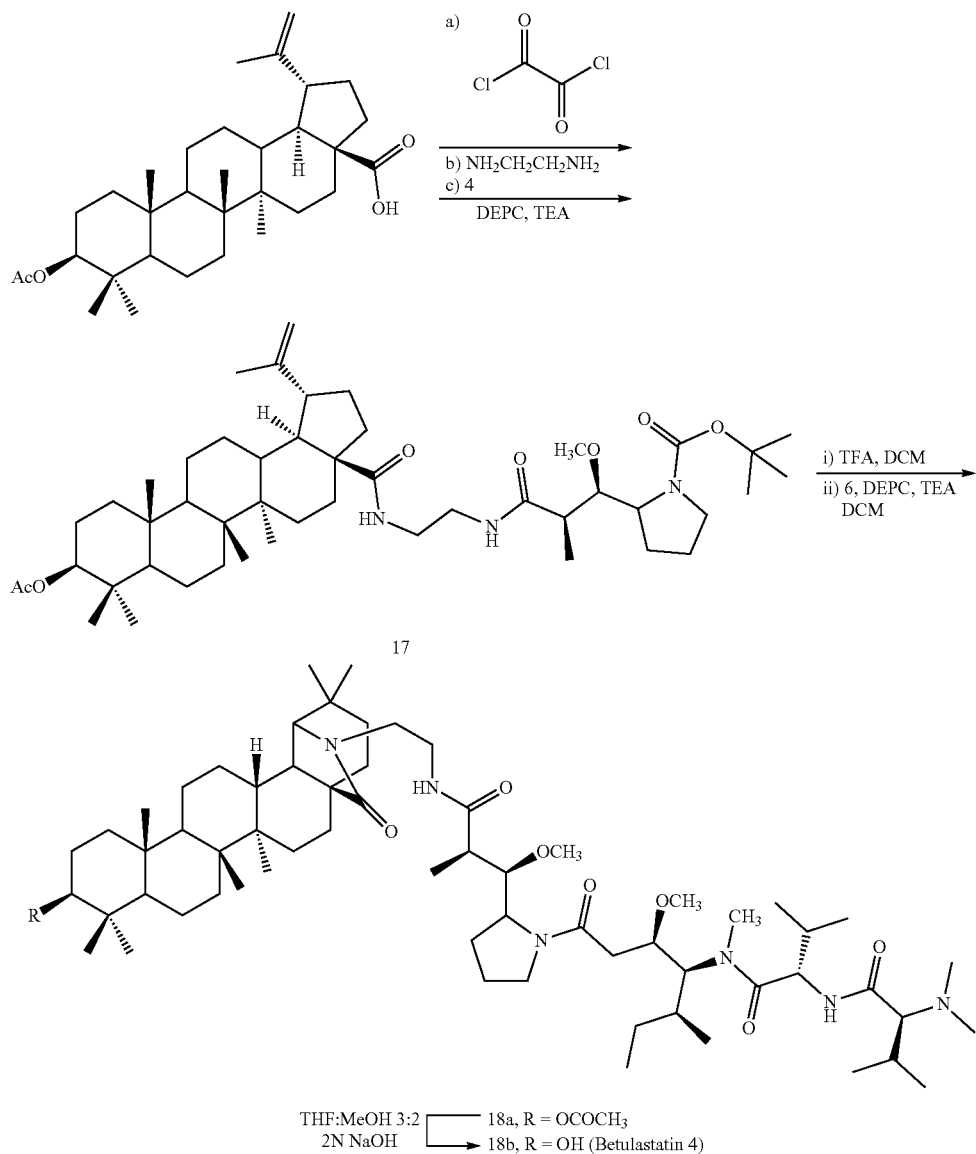

3-O-Acetyl-28-amido-allobetulin-28-N-1'-ethyldiamine-N-2'-Dap-Dil-Val-Dov (18a). Betulinic acid and 3-O-Acetyl-betulinic acid were prepared as previously described.[8] 3-O-Acetyl-betulinic acid (0.113 g, 0.2 mmol) and oxalyl chloride (2 M in $CH_2Cl_2$) (1 mL, 2 mmol) were stirred together for 10 min then concentrated under vacuum to remove excess reagent. The residue was dissolved in $CH_2Cl_2$ (2 mL) and diethylamine (0.15 mL) was added. The mixture was stirred at rt under $N_2$ for 5 h, the solution was concentrated and water added. The resulting white precipitate was collected, washed with water, dissolved in ethanol and filtered. The ethanol solution was then concentrated to a light yellow colored residue which was dried under reduced pressure. The residue (0.08 g, 0.15 mmol) was dissolved in anhydrous $CH_2Cl_2$ (2 ml) and a solution of Boc-Dap (0.043 g, 0.15 mmol, 1 equiv.) in $CH_2Cl_2$ (2 mL) was added. The solution was cooled in an ice bath and TEA (60 μL, 3.5 equiv) followed by DEPC (0.036 mL, 1.5 equiv) was added. The reaction mixture was stirred for 24 h under $N_2$ and allowed to warm to rt overtime, before concentrating and separating on silica gel by eluting with hexanes-ethyl acetate (8:2) followed by hexane-acetone (7:3), yielded Boc protected amide 17 as a colorless solid, 78 mg; TLC $R_f$ 0.14 (Hexane:$CH_3COCH_3$ 4:1); mp 135° C.; (+)-HRAPCIMS m/z 810.5978 [M+H]$^+$ (calcd. for $C_{48}H_{80}N_3O_7$, 810.59 96). The Boc protected amide 17 was used directly in the next step. Boc protected amide 17 (0.077 g, 0.096 mmol) was dissolved in anhydrous $CH_2Cl_2$ (4 mL) and the solution was cooled (ice bath). TFA (1.5 mL) was added and the reaction was stirred for 1 h then concentrated under reduced pressure overnight. The TFA salt was dissolved in $CH_2Cl_2$ (4 mL) and Dov-Val-Dil-TFA (0.05 g) was added. The reaction mixture was cooled (ice bath) and TEA (0.06 mL) and DEPC (0.02 mL) were added, then stirred under nitrogen for 24 h with warming to rt. Concentration to a yellow oil followed by separation on silica gel (gradient elution: Hexanes-$CH_3COCH_3$ 7:3→6.5→4:5), gave 18a as a colorless solid (32 mg, 18% yield from Boc-dap): mp 114-115° C.; TLC $R_f$ 0.4 (Hexanes:$CH_3COCH_3$ 4:6); $^1H$ NMR (CDCl$_3$, 400 MHz) δ 6.85 (1H, d, J=9.0 Hz), 6.51 (1H, m), 4.88, 4.69 (0.5H, 1H, m), 4.42 (1H, m), 4.19-4.06 (2H, m), 3.91 (1H, m), 3.82-3.72 (2H, m), 3.52-3.22 (13H, m), 3.37, 3.29 (s, OCH$_3$), 2.99, 3.10 (3H, s, NCH$_3$), 2.48-2.34 (3H, m), 2.22 (6H, s, N(CH$_3$)$_2$, 1.83-0.73 (CH, CH$_2$ and CH$_3$ protons); $^{13}C$ (CDCl$_3$, 100 MHz), δ 173.9, 171.9, 171.8, 171.2, 170.3, 170.2, 82.5, 81.0, 76.8, 76.7, 61.9, 61.8, 60.4, 59.2, 59.0, 58.3 58.2, 55.8, 54.0, 53.9, 51.3, 47.8, 47.1, 47.05, 46.8, 45.9, 45.7, 45.3, 45.2, 43.8, 43.1, 43.0, 40.7, 40.4, 40.3, 38.8, 38.0, 37.9, 37.4, 35.9, 35.8, 34.5, 34.3, 34.2, 33.9, 33.4, 32.7, 31.2, 31.1, 29.5, 29.1, 28.1, 27.9, 27.4, 26.5, 26.3, 25.9, 25.3, 25.0, 24.3, 24.2, 23.8, 21.5, 21.1, 20.3, 18.3, 18.0, 17.9, 16.7, 16.6, 15.7, 15.69, 15.6, 14.1, 13.9, 11.0; (+)-HRAPCIMS m/z 1121.8560 (calcd. for $C_{65}H_{113}N_6O_9$, 1121.857).

28-Amido-allobetulin-28-N-1'-ethyldiamine-N-2'-Dap-Dil-Val-Dov (18b). To a solution of peptide 18a (0.012 g, 0.011 mmol) in a mixture of THF:MeOH (1.4 mL, 0.8:0.6), 2N NaOH (0.3 mL) was added. The solution was stirred at rt for 24 h. The solvent was evaporated and the residue separated on a silica gel column eluting with $CH_2Cl_2$:$CH_3OH$ 95%:5% to give the C-3 deprotected product as a colorless solid, 2 mg (17% yield): TLC $R_f$ 0.13 (DCM: MeOH 92%:8%). $^1H$ NMR (CDCl$_3$, 500 MHz) conformational isomers observed δ 6.94, 6.89 (1H, d, J=9.0 Hz), 6.51, 6.14 (1H, m), 4.95-4.70 (2H, m), 4.25-4.10 (2H, m), 3.96 (1H, m), 3.82 (1H, m), 3.57-3.28 (13H, m), 3.42, 3.41, 3.34, 3.33 (s, OCH$_3$), 3.21 (1H, dd, J=12, 4 Hz), 3.14, 3.03 (3H, s, NCH$_3$), 2.63-2.38 (4H, m), 2.36-2.22 (7H, m) 2.27, 2.26 (s, N(CH$_3$)$_2$, 2.19-1.96 (5H, m), 1.87-0.80 (CH, CH$_2$ and CH$_3$ protons), 0.78 (3H, s, CH$_3$), 0.70 (1H, m); (+)-HRESIMS m/z 1079.8472 (calcd. for $C_{63}H_{111}N_6O_8$, 1079.8458).

Example 5—Inhibition of Human Cancer Cell Growth

Cancer Cell Line Procedures. Inhibition of human cancer cell growth was assessed using the standard sulforhodamine B assay of the U.S. National Cancer Institute, as previously described.[15] To begin, cells in a 5% fetal bovine serum/RPMI1640 medium were inoculated in 96-well plates and incubated for 24 h. Next, serial dilutions of the compounds were added. After 48 h, the plates were fixed with trichloroacetic acid, stained with sulforhodamine B, and read with an automated microplate reader. A growth inhibition of 50% (GI$_{50}$ or the drug concentration causing a 50% reduction in the net protein increase) was calculated from optical density data with Immunosoft® software.

TABLE 1

Human Cancer Cell Lines (GI$_{50}$ μg/mL in DMSO) Growth Inhibition Results from Comparison Experiments.

| compound | cell line[a] | | | | | |
|---|---|---|---|---|---|---|
| | XPC-3 | MCF-7 | SF-268 | NCI-H460 | KM20L2 | DU-145 |
| Betulin[b,5] | 9.3 | >10 | >10 | 7.4 | >10 | >10 |
| 1 | >10 | >10 | >10 | >10 | >10 | >10 |
| 2 | 15.5 | 4.5 | 13.2 | 4.1 | 5.1 | >10 |
| 3 | 1.9 | 1.8 | 1.8 | 1.9 | 1.9 | 1.8 |
| 5 | >10 | >10 | >10 | >10 | >10 | >10 |
| 7a | 4.1 | 3.6 | 2.6 | 4.2 | 2.4 | 3.7 |
| 7b | 0.60 | 0.40 | 0.30 | >1 | 0.31 | 0.40 |
| 8 | 10.4 | 5.9 | >10 | >10 | 14.1 | >10 |
| 9a | >10 | 2.1 | 1.2 | 6.0 | 3.0 | 1.3 |
| 9b | 1.1 | 0.20 | 0.21 | 0.21 | 0.35 | 0.13 |
| 10 | >10 | >10 | >10 | >10 | >10 | >10 |
| 11a | 10.0 | 4.1 | 3.8 | >10 | 7.0 | 2.5 |
| 11b | 2.0 | 0.70 | 0.40 | 2.1 | 0.85 | 0.40 |
| 12 | >10 | >10 | >10 | >10 | >10 | >10 |
| 13 | >10 | >10 | >10 | >10 | >10 | >10 |
| 14 | 3.0 | 3.1 | 4.2 | 4.0 | 2.9 | 2.1 |
| 15a | >10 | 9.0 | >10 | >10 | >10 | >10 |
| 15b | >10 | >10 | 5.9 | >10 | 7.0 | >10 |
| 16a | 8.0 | 6.3 | 4.0 | >10 | 4.0 | 3.0 |
| 16b | 0.40 | 0.08 | 0.04 | 0.50 | 0.090 | 0.040 |
| 18a | 3.8 | 3.6 | 1.3 | 5.1 | 3.1 | 0.39 |
| 18b | 0.31 | 0.21 | 0.09 | 0.60 | 0.22 | 0.06 |

[a]Cancer cell lines in order: pancreas (BXPC-3); breast (MCF-7); CNS (SF-268); lung (NCI-H460); colon (KM20L2); prostate (DU-145).
[b]Source: Sigma-Aldrich.

Chimera 7b, amine 9b, chimeras 11b and 18b in general resulted in a 10-fold increase in cancer cell growth while chimera 16b provided a hundred-fold increase.

REFERENCES

The following references are hereby incorporated by reference in their entireties:
(1) For Antineoplastic Agents 605 refer to reference 1b. (b) Pettit, G. R.; Melody, N.; Chapuis, J.-C. *J. Nat. Prod.* Submitted
(2) (a) Tsepaeva, O. V.; Nemtarev, A. V.; Abdullin, T. I.; Grigor'eva, L. R.; Kuznetsova, E. V.; Akhmadishina, R. A.; Ziganshina, L. E.; Cong, H. H.; Mironov, V. F. *J. Nat. Prod.* 2017, 80, 2232-2239. (b) Ali-Seyed, M.; Jantan, I.; Vijayaraghavan, K.; Bukhari, S. N. A. *Chem. Biol. Drug Des.,* 2016, 87, 517-536. (c) Zhang, D.-M.; Xu, H.-G.; Wang, L.; Li, Y.-J.; Sun, P.-H.; Wu, X.-M.; Wang, G.-J., Chen, W.-M.; Ye, W.-C. *Med. Res. Revs,* 2015, 35 (6), 1127-1155. (d) Król, S. K.; Kiełbus, M.; Rivero-Müller, A.; Stepulak, A.; *BioMed Research Int.* 2015, Article ID 584189, 1-11. (e) Rastogi, S.; Pandey, M. M.; Rawat, S. K. A.; *J. EthnoPharma.,* 2015, 159, 62-83. (f) Periasamy, G.; Teketelew, G.; Gebrelibanos, M.; Sintayehu, B.; Gebrehiwor, M.; Karim, A.; Geremedhin, G.; *Archvs. App. Sci. Res.* 2014, 6 (3), 47-58.
(3) Pettit, G. R.; Melody, N.; Hempenstal, F., Chapuis, J.-C.; Groy. T. L.; Williams, L. *J. Nat. Prod.* 2014, 77, 863-872.
(4) Pettit, G. R.; Green, B.; Bowyer, W. J. *J. Org. Chem.* 1961, 26, 2879
(5) Pettit, G. R.; Klinger, H.; Jorgensen, N.-O. N. *Phytochemistry,* 1966, 5, 301-309 (b) Cháirez-Ramírez, M. H.; Moreno-Jiménez, M. R.; González-Laredo, R. F.; Gallegos-Infante, J. A.; Rocha-Guzmán, N. E.; *EXCLI J.* 2016, 15, 758-771. (c) Silva, F. S. G.; Oliveira, P. J.; Duarte, M. F.; *J. Agric. Food. Chem.* 2016, 64, 2999-3008. (d) Salvador, J. A. R.; Leal, A. S.; Alho, D. P. S.; Gonçalves, B. M. F.; Valdeira, A. S.; Mendes, V. I. S.; Jing, Y. *Studies in Nat. Prods. Chem.* 2014, 41(2), 33-63.

(6) Pettit G. R.; Kamano, Y.; Hearld, C. L.; Tuinman, A. A.; Boettner, F. E.; Kizu, H.; Schmidt, J. M.; Baczynsyi, L.; Tomer, K. B.; Botems, R. J. *J. Am. Chem. Soc.,* 1987, 109, 6883-6885.

(7) (a) Xu, Y-C; Bizuneh, A.; Walker, C.; *J. Org. Chem.* 1996, 61, 9086-9089. (b) Thibeault, D., Gauthier, C., Legault, J., Bouchard, J., Dufour, P., Pichette, A., *Bioorg. Med. Chem.* 2007, 15, 6144-6157. (c) Santos, R. C.; Salvador, J. A. R.; Marin, S.; Cascante, M.; Moreira, J. N.; Dinis, T. C. P. *Bioorg. Med. Chem.* 2010, 18, 4385-4396.

(8) Flekhter, O. B.; Ashavina, O. Y.; Boreko, E. I.; Karachurina, L. T.; Pavlova, N. I.; Kabal'nova, N. N.; Savinova, O. V.; Galin, F. Z.; Nikolaeva, S. N.; Zarudii, F. S.; Baltina, L. A.; and Tolstikov, G. A. *Pharma. Chem. J.* 2002, 36 (6), 303-306.

(9) (a) Leeds, J. P.; Kirst, H. A. *Syn. Comm.* 1988, 18 (8) 777-782. (b) Kim, D. S. H. L.; Pezzuto, J. M.; Pisha, E. *Biorg. Med. Chem. Lett.* 1998, 8, 1707-1712.

(10) (a) Pettit, G. R.; Singh, S. B.; Herald, D. L.; Lloyd-Williams, P.; Kantoci, D.; Burkett, D. D.; Barkóczy, J.; Hogan, F.; Wardlaw, T. R. *J. Org. Chem.* 1994, 59, 6287-6295. (b) Pettit, G. R.; Grealish, M. P.; *J. Org. Chem.* 2001, 66, 8640-8642.

(11) Pettit, G. R.; Srirangam, J. K.; Singh, S. B.; Williams, M. D.; Herald, D. L.; Barkóczy, J.; Kantoci, D.; Hogan, F. *J Chem. Soc., Perkin Trans.* 1, 1996, 859-863.

(12) Klinotová, E., Křeček, V., Klinot, J., Endová, M., Eisenreichová, J., Buděšinský, M., Šticha, M. Collect. *Czech. Chem. Commun.,* 1997, 62, 1776-1798.

(13) Sun, I.-C.; Wang, H.-K.; Kashiwada, Y.; Shen, J.-K.; Cosentino, L. M.; Chen, C.-H.; Yang, L.-M.; Lee, K.-H., *J. Med. Chem.* 1998, 41, 4648-4657.

(14) Antimonova, A. N.; Petrenko, N. I.; Shakirov, M. M.; Rybalova, T. V.; Frolova, T. S.; Shultz, E. E.; Kukina, T. P.; Sinitsyna, O. I.; Tostikov, G. A.; *Chem. Nat. Compds.,* 2013, 49(4), 657-664.

(15) Monks, A.; Scudiero, D.; Skehan, P.; Shoemaker, R.; Paull, K.; Vistica, D.; Hose, C.; Langley, J.; Cronise, P.; Viagro-Wolff, A.; Gray-Goodrich, M.; Campbell, H.; Mayo, J.; Boyd, M. *J. Natl. Cancer Inst.* 1991, 83, 757-766.

(16) Tsepaeva, O; Nemtarev, A.; Abdullin, T.; Grigor'eva, L; Kuznetsova, E.; Akhmadishina, R.; Ziganshina, L.; Cong, H.; Mironov, V. *J. Nat. Prod.* 2017, 80, 2232-2239.

While particular materials, formulations, operational sequences, process parameters, and end products have been set forth to describe and exemplify this invention, they are not intended to be limiting. Rather, it should be noted by those ordinarily skilled in the art that the written disclosures are exemplary only and that various other alternatives, adaptations, and modifications may be made within the scope of the present invention. Accordingly, the present invention is not limited to the specific embodiments illustrated herein, but is limited only by the following claims.

What is claimed is:

1. A compound of formula (II)

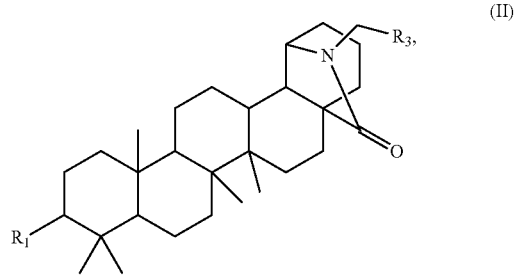

or a pharmaceutically acceptable salt thereof, wherein
$R_1$ is OH, OCOCH$_3$, O—P(=O)OR'OR", or O-Protecting Group, wherein R' and R" are independently selected from the group consisting of lithium (Li$^+$), sodium (Na$^+$), potassium (K$^+$), hydrogen (H), morpholine, quinine, tris(hydroxymethyl)aminomethane (TRIS), serine, and nitroarginine;
$R_3$ is $R_4$ or $R_6$-$R_4$;
$R_4$ is

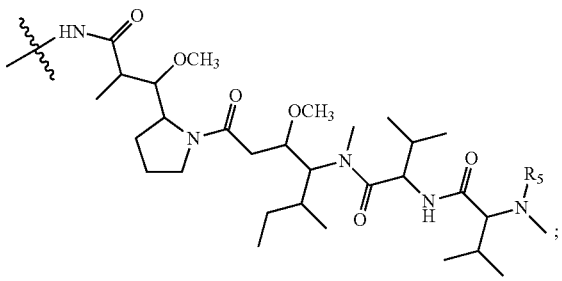

$R_5$ is H or (C$_1$-C$_6$)alkyl; and
$R_6$ is (C$_1$-C$_6$)alkyl.

2. The compound of claim 1, wherein $R_1$ is OH, OCOCH$_3$, or O—P(=O)OR'OR".

3. The compound of claim 1, wherein $R_1$ is OH.

4. The compound of claim 1, wherein $R_1$ is OCOCH$_3$.

5. The compound of claim 1, wherein $R_3$ is $R_4$.

6. The compound of claim 1, wherein $R_5$ is CH$_3$.

7. The compound of claim 1, wherein $R_3$ is $R_6$-$R_4$.

8. The compound of claim 7, wherein $R_5$ is CH$_3$.

9. The compound of claim 1, wherein the compound is selected from the group consisting of:

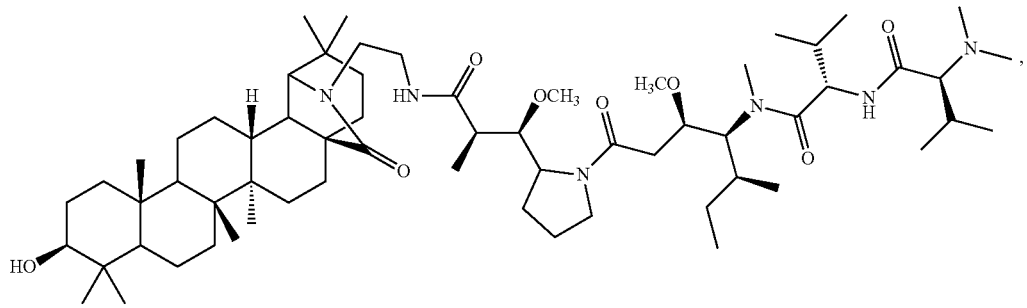

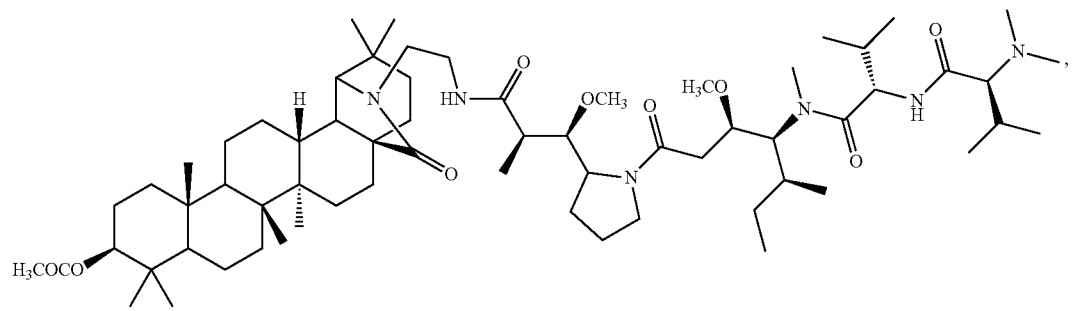
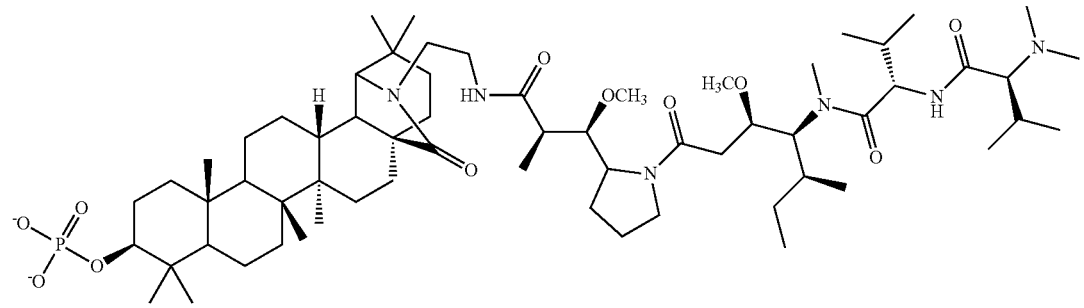
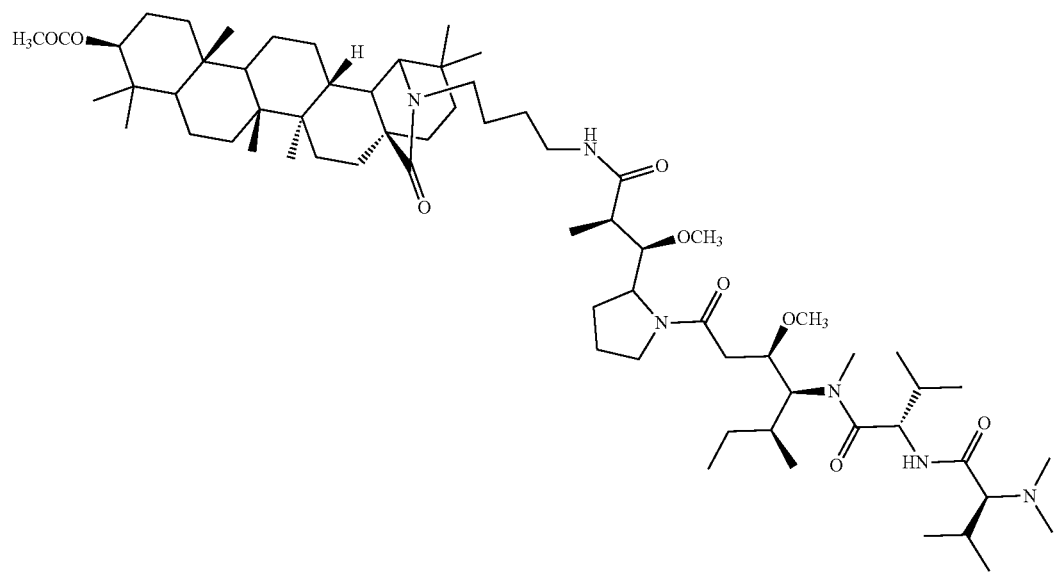
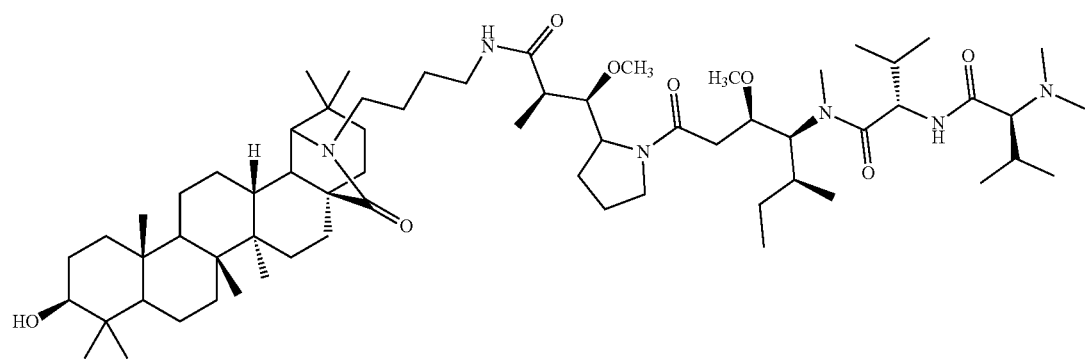
and

-continued

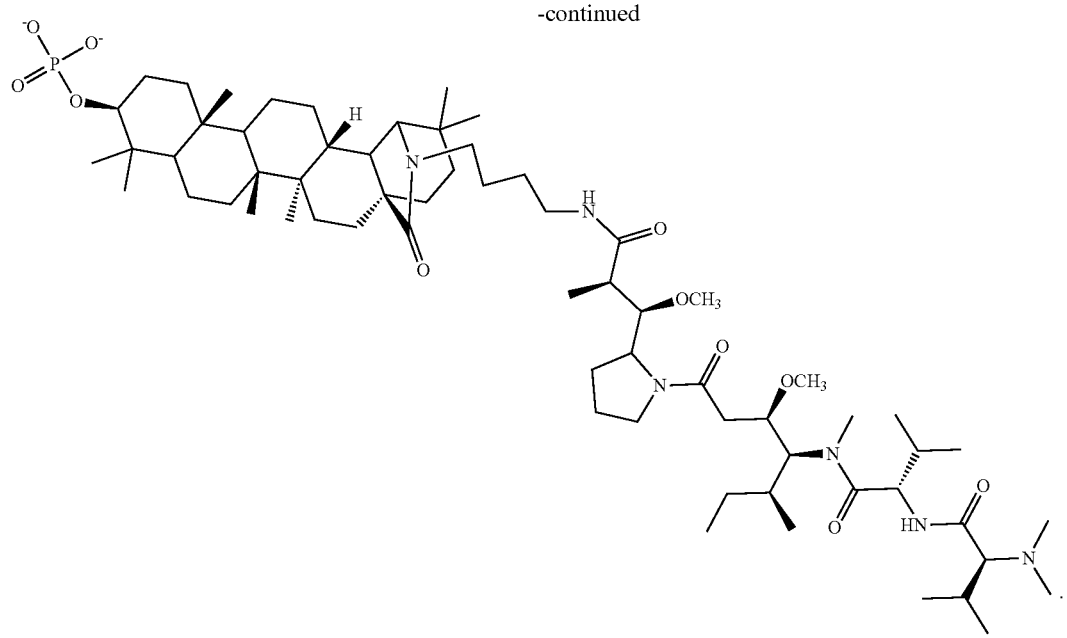

10. A pharmaceutical composition comprising a compound of claim 1 or a pharmaceutically acceptable salt thereof and a pharmaceutically acceptable carrier.

11. A pharmaceutical composition comprising a combination of compounds of claim 1 or pharmaceutically acceptable salts thereof and a pharmaceutically acceptable carrier.

12. The pharmaceutical composition of claim 10 further comprising a second therapeutic agent selected from the group consisting of a tubulin-forming inhibitor, a topoisomerase inhibitor, and a DNA binder.

13. A method for killing or inhibiting the proliferation of tumor cells or cancer cells comprising treating the tumor cells or cancer cells with a compound of claim 1, in an amount effective to kill or inhibit the proliferation of the tumor cells or cancer cells, wherein the tumor cells or cancer cells are at least one selected from the group consisting of pancreas, breast, glioblastoma multiforme, lung, colon, and prostate cells.

14. A method for treating cancer in a patient in need thereof comprising administering to the patient a compound of claim 1, wherein the compound is administered in an amount effective to treat cancer, wherein the cancer selected from the group consisting of pancreas, breast, glioblastoma multiforme, lung, colon, and prostate cancer.

15. The method of claim 14, further comprising administering an effective amount of a second therapeutic agent.

16. An in vitro method of determining inhibition of cellular proliferation by a compound, comprising contacting cells in a cell culture medium with the compound of claim 1 and measuring the cytotoxic activity of the compound, whereby proliferation of the cells is inhibited.

* * * * *